(12) United States Patent
D'Aquanni et al.

(10) Patent No.: US 7,942,892 B2
(45) Date of Patent: May 17, 2011

(54) RADIOPAQUE NITINOL EMBOLIC PROTECTION FRAME

(75) Inventors: Peter D'Aquanni, Murrieta, CA (US);
John F. Boylan, Murrieta, CA (US);
Wayne E. Cornish, Fallbrook, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 10/427,576

(22) Filed: May 1, 2003

(65) Prior Publication Data
US 2004/0220608 A1 Nov. 4, 2004

(51) Int. Cl.
*A61M 29/00* (2006.01)
(52) U.S. Cl. ......... 606/200; 606/159; 606/191; 606/198
(58) Field of Classification Search .................. 623/1.11, 623/1.23; 606/200, 108; 604/96.01, 103.01, 604/97.01
See application file for complete search history.

(56) References Cited

U.S. PATENT DOCUMENTS

| | | | |
|---|---|---|---|
| 2,738,294 A | 3/1956 | Spence | |
| 2,768,271 A | 10/1956 | Meredith | |
| 3,558,369 A | 1/1971 | Wang et al. | |
| 3,605,725 A | 9/1971 | Bentov | |
| 3,620,212 A | 11/1971 | Fannon et al. | |
| 3,753,700 A | 8/1973 | Harrison et al. | |
| 3,890,977 A | 6/1975 | Wilson | |
| 3,953,253 A | 4/1976 | Clark | |
| 4,019,899 A | 4/1977 | Negishi et al. | |
| 4,037,324 A | 7/1977 | Andreasen | |
| 4,069,226 A | 1/1978 | Kablaoui et al. | |
| 4,144,057 A | 3/1979 | Melton et al. | |
| 4,233,690 A | 11/1980 | Akins | |
| 4,283,233 A | 8/1981 | Goldstein et al. | |
| 4,304,613 A | 12/1981 | Wang et al. | |
| 4,310,354 A | 1/1982 | Fountain et al. | |
| 4,323,071 A | 4/1982 | Simpson et al. | |
| 4,386,971 A | 6/1983 | Melton et al. | |
| 4,390,599 A | 6/1983 | Broyles | |
| 4,411,655 A | 10/1983 | Schreck | |
| 4,425,908 A | 1/1984 | Simon | |
| 4,427,000 A | 1/1984 | Ueda | |

(Continued)

FOREIGN PATENT DOCUMENTS

EP 0145166 6/1985

(Continued)

OTHER PUBLICATIONS

Russel et al.: "Improved NiTi Alloys for Medical Applications" 1997, pp. 429-436.*

(Continued)

*Primary Examiner* — Corrine M McDermott
*Assistant Examiner* — Christopher D Prone
(74) *Attorney, Agent, or Firm* — Workman Nydegger; Jonathan D. Feuchtwang

(57) ABSTRACT

An expandable frame for an embolic filtering device used to capture embolic debris in a body lumen. The expandable frame also includes a filtering element. A nickel-titanium alloy is used to form the frame. Due to limited heat treatment, the frame exhibits linear pseudoelasticity when positioned inside the body lumen. The nickel-titanium alloy includes a ternary element such as iridium, platinum, gold, rhenium, tungsten, palladium, rhodium, tantalum, silver, ruthenium, or hafnium so that the frame is also radiopaque.

16 Claims, 5 Drawing Sheets

U.S. PATENT DOCUMENTS

| | | |
|---|---|---|
| 4,439,185 A | 3/1984 | Lundquist |
| 4,503,569 A | 3/1985 | Dotter |
| 4,505,767 A | 3/1985 | Quin |
| 4,512,338 A | 4/1985 | Balko et al. |
| 4,516,972 A | 5/1985 | Samson |
| 4,518,444 A | 5/1985 | Albrecht et al. |
| 4,533,411 A | 8/1985 | Melton |
| 4,538,622 A | 9/1985 | Samson et al. |
| 4,554,929 A | 11/1985 | Samson et al. |
| 4,565,589 A | 1/1986 | Harrison |
| 4,580,568 A | 4/1986 | Gianturco |
| 4,582,181 A | 4/1986 | Samson |
| 4,616,652 A | 10/1986 | Simpson |
| 4,631,094 A | 12/1986 | Simpson et al. |
| 4,638,805 A | 1/1987 | Powell |
| 4,665,906 A | 5/1987 | Jervis |
| 4,740,253 A | 4/1988 | Simpson et al. |
| 4,748,986 A | 6/1988 | Morrison et al. |
| 4,768,507 A | 9/1988 | Fischell et al. |
| 4,770,725 A | 9/1988 | Simpson et al. |
| 4,776,844 A | 10/1988 | Ueda |
| 4,793,350 A | 12/1988 | Mar et al. |
| 4,827,941 A | 5/1989 | Taylor et al. |
| 4,846,573 A | 7/1989 | Taylor et al. |
| 4,856,516 A | 8/1989 | Hillstead |
| 4,865,663 A | 9/1989 | Tuominen et al. |
| 4,875,489 A | 10/1989 | Messner et al. |
| 4,881,981 A | 11/1989 | Thoma et al. |
| 4,894,100 A | 1/1990 | Yamauchi et al. |
| 4,925,445 A | 5/1990 | Sakamoto et al. |
| 4,935,068 A | 6/1990 | Duerig |
| 4,943,326 A | 7/1990 | Ozawa et al. |
| 4,969,890 A | 11/1990 | Sugita et al. |
| 4,984,581 A | 1/1991 | Stice |
| 4,991,602 A | 2/1991 | Amplatz et al. |
| 5,001,446 A | 3/1991 | Tsuji et al. |
| 5,002,563 A | 3/1991 | Pyka et al. |
| 5,025,799 A | 6/1991 | Wilson |
| 5,044,947 A | 9/1991 | Sachdeva et al. |
| 5,067,489 A | 11/1991 | Lind |
| 5,067,957 A | 11/1991 | Jervis |
| 5,069,226 A | 12/1991 | Yamauchi et al. |
| 5,092,877 A | 3/1992 | Pinchuk |
| 5,108,523 A | 4/1992 | Peterseim et al. |
| 5,114,504 A | 5/1992 | AbuJudom, II et al. |
| 5,117,838 A | 6/1992 | Palmer et al. |
| 5,120,308 A | 6/1992 | Hess |
| 5,135,503 A | 8/1992 | Abrams |
| 5,143,085 A | 9/1992 | Wilson |
| 5,171,383 A | 12/1992 | Sagae et al. |
| 5,188,621 A | 2/1993 | Samson |
| 5,190,546 A | 3/1993 | Jervis |
| 5,201,901 A | 4/1993 | Harada et al. |
| 5,230,348 A | 7/1993 | Ishibe et al. |
| 5,230,349 A | 7/1993 | Langberg |
| 5,234,458 A | 8/1993 | Metais |
| 5,238,004 A | 8/1993 | Sahatjian et al. |
| 5,243,996 A | 9/1993 | Hall |
| 5,271,975 A | 12/1993 | Solano |
| 5,292,331 A | 3/1994 | Boneau |
| 5,318,527 A | 6/1994 | Hyde et al. |
| 5,341,815 A | 8/1994 | Cofone et al. |
| 5,341,818 A | 8/1994 | Abrams et al. |
| 5,345,937 A | 9/1994 | Middleman et al. |
| 5,345,945 A | 9/1994 | Hodgson et al. |
| 5,350,398 A | 9/1994 | Pavcnik et al. |
| 5,350,419 A | 9/1994 | Bendel et al. |
| 5,354,623 A | 10/1994 | Hall |
| 5,368,049 A | 11/1994 | Raman et al. |
| 5,411,476 A | 5/1995 | Abrams et al. |
| 5,458,615 A | 10/1995 | Klemm et al. |
| 5,465,717 A | 11/1995 | Imran et al. |
| 5,486,183 A | 1/1996 | Middleman et al. |
| 5,507,766 A | 4/1996 | Kugo et al. |
| 5,509,923 A | 4/1996 | Middleman et al. |
| 5,514,154 A | 5/1996 | Lau et al. |
| 5,534,007 A | 7/1996 | St. Germain et al. |
| 5,549,626 A | 8/1996 | Miller et al. |
| 5,562,641 A | 10/1996 | Flomenblit et al. |
| 5,569,295 A | 10/1996 | Lam |
| 5,573,520 A | 11/1996 | Schwartz et al. |
| 5,597,378 A | 1/1997 | Jervis |
| 5,607,444 A | 3/1997 | Lam |
| 5,611,874 A | 3/1997 | Zadno-Azizi et al. |
| 5,630,840 A | 5/1997 | Mayer |
| 5,632,746 A | 5/1997 | Middleman et al. |
| 5,637,089 A | 6/1997 | Abrams et al. |
| 5,641,364 A | 6/1997 | Golberg et al. |
| 5,643,312 A | 7/1997 | Fischell et al. |
| 5,667,522 A | 9/1997 | Flomenblit et al. |
| 5,690,644 A | 11/1997 | Yurek et al. |
| 5,695,111 A | 12/1997 | Nanis et al. |
| 5,713,853 A | 2/1998 | Clark et al. |
| 5,720,300 A | 2/1998 | Fagan et al. |
| 5,720,754 A | 2/1998 | Middleman et al. |
| 5,749,370 A | 5/1998 | Brooks et al. |
| 5,749,870 A | 5/1998 | Gloth et al. |
| 5,749,879 A | 5/1998 | Middleman et al. |
| 5,759,192 A | 6/1998 | Saunders |
| 5,766,218 A | 6/1998 | Arnott |
| 5,776,114 A | 7/1998 | Frantzen et al. |
| 5,780,807 A | 7/1998 | Saunders |
| 5,810,874 A | 9/1998 | Lefebvre |
| 5,820,628 A | 10/1998 | Middleman et al. |
| 5,833,631 A | 11/1998 | Nguyen |
| 5,836,966 A | 11/1998 | St. Germain |
| 5,836,968 A | 11/1998 | Simon et al. |
| 5,837,313 A | 11/1998 | Ding et al. |
| 5,843,244 A | 12/1998 | Pelton et al. |
| 5,865,768 A | 2/1999 | Orr |
| 5,876,356 A | 3/1999 | Viera et al. |
| 5,876,434 A | 3/1999 | Flomenblit et al. |
| 5,885,381 A | 3/1999 | Mitose et al. |
| 5,891,191 A | 4/1999 | Stinson |
| 5,902,317 A | 5/1999 | Kleshinski et al. |
| 5,904,690 A | 5/1999 | Middleman et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,922,393 A | 7/1999 | Jayaraman |
| 5,927,345 A | 7/1999 | Samson |
| 5,931,819 A | 8/1999 | Fariabi |
| 5,951,793 A | 9/1999 | Mitose et al. |
| 5,964,770 A | 10/1999 | Flomenblit et al. |
| 5,976,153 A | 11/1999 | Fischell et al. |
| 5,980,471 A | 11/1999 | Jafari |
| 5,980,566 A | 11/1999 | Alt et al. |
| 5,989,280 A | 11/1999 | Euteneuer et al. |
| 6,001,123 A | 12/1999 | Lau |
| 6,004,330 A | 12/1999 | Middleman et al. |
| 6,004,629 A | 12/1999 | Madigan |
| 6,007,558 A | 12/1999 | Ravenscroft et al. |
| RE36,628 E | 3/2000 | Sagae et al. |
| 6,051,021 A | 4/2000 | Frid |
| 6,053,992 A | 4/2000 | Wu et al. |
| 6,059,738 A | 5/2000 | Stoltze et al. |
| 6,059,810 A | 5/2000 | Brown et al. |
| 6,066,149 A | 5/2000 | Samson et al. |
| 6,068,610 A | 5/2000 | Ellis et al. |
| 6,068,623 A | 5/2000 | Zadno-Azizi et al. |
| 6,077,287 A | 6/2000 | Taylor et al. |
| 6,077,295 A | 6/2000 | Limon et al. |
| 6,086,610 A * | 7/2000 | Duerig et al. ............... 623/1.18 |
| 6,096,175 A | 8/2000 | Roth |
| 6,099,549 A | 8/2000 | Bosma et al. |
| 6,106,642 A | 8/2000 | DiCarlo et al. |
| 6,129,739 A * | 10/2000 | Khosravi ...................... 606/200 |
| 6,131,266 A | 10/2000 | Saunders |
| 6,137,060 A | 10/2000 | Avellanet |
| 6,152,946 A | 11/2000 | Broome et al. |
| 6,165,140 A | 12/2000 | Ferrera |
| 6,165,195 A | 12/2000 | Wilson et al. |
| 6,165,292 A | 12/2000 | Abrams et al. |
| 6,168,571 B1 | 1/2001 | Solar et al. |
| 6,171,327 B1 | 1/2001 | Daniel et al. |
| 6,171,334 B1 | 1/2001 | Cox |
| 6,179,859 B1 | 1/2001 | Bates et al. |

| | | |
|---|---|---|
| 6,183,409 B1 | 2/2001 | Armini |
| 6,190,332 B1 | 2/2001 | Muni et al. |
| 6,210,312 B1 | 4/2001 | Nagy |
| 6,217,567 B1 | 4/2001 | Zadno-Azizi et al. |
| 6,217,589 B1 | 4/2001 | McAlister |
| 6,245,103 B1 | 6/2001 | Stinson |
| 6,257,513 B1 | 7/2001 | Cockerham et al. |
| 6,264,671 B1 | 7/2001 | Stack et al. |
| 6,277,139 B1 | 8/2001 | Levinson et al. |
| 6,280,539 B1 | 8/2001 | Abrams et al. |
| 6,287,336 B1 | 9/2001 | Globerman et al. |
| 6,306,141 B1 | 10/2001 | Jervis |
| 6,312,454 B1 | 11/2001 | Stöckel et al. |
| 6,312,455 B2 | 11/2001 | Duerig et al. |
| 6,322,847 B1 | 11/2001 | Zhong et al. |
| 6,325,824 B2 | 12/2001 | Limon |
| 6,329,069 B1 | 12/2001 | Azizi et al. |
| 6,346,116 B1 | 2/2002 | Brooks et al. |
| 6,352,515 B1 | 3/2002 | Anderson et al. |
| 6,358,556 B1 | 3/2002 | Ding et al. |
| 6,371,970 B1 | 4/2002 | Khosravi et al. |
| 6,375,458 B1 | 4/2002 | Moorleghem et al. |
| 6,375,628 B1 | 4/2002 | Zadno-Azizi et al. |
| 6,375,629 B1 | 4/2002 | Muni et al. |
| 6,379,369 B1 | 4/2002 | Abrams et al. |
| 6,380,457 B1 | 4/2002 | Yurek et al. |
| 6,390,993 B1 | 5/2002 | Cornish et al. |
| 6,391,502 B1 | 5/2002 | Anderson et al. |
| 6,402,761 B2 | 6/2002 | McAlister |
| 6,419,692 B1 | 7/2002 | Yang et al. |
| 6,419,693 B1 | 7/2002 | Fariabi |
| 6,428,634 B1 | 8/2002 | Besselink et al. |
| 6,432,116 B1 | 8/2002 | Callister et al. |
| 6,447,523 B1 | 9/2002 | Middleman et al. |
| 6,451,047 B2 | 9/2002 | McCrea et al. |
| 6,451,052 B1 | 9/2002 | Burmeister et al. |
| 6,458,145 B1 | 10/2002 | Ravenscroft et al. |
| 6,461,453 B1 | 10/2002 | Abrams et al. |
| 6,468,230 B2 | 10/2002 | Muni et al. |
| 6,500,182 B2 | 12/2002 | Foster |
| 6,508,803 B1 | 1/2003 | Horikawa et al. |
| 6,509,094 B1 | 1/2003 | Shah et al. |
| 6,533,805 B1 | 3/2003 | Jervis |
| 6,551,341 B2* | 4/2003 | Boylan et al. ................ 606/200 |
| 6,554,848 B2 | 4/2003 | Boylan et al. |
| 6,558,405 B1 | 5/2003 | McInnes |
| 6,572,646 B1 | 6/2003 | Boylan et al. |
| 6,582,461 B1 | 6/2003 | Burmeister et al. |
| 6,592,559 B1 | 7/2003 | Pakter et al. |
| 6,592,570 B2 | 7/2003 | Abrams et al. |
| 6,602,208 B2 | 8/2003 | Jafari |
| 6,602,228 B2 | 8/2003 | Nanis et al. |
| 6,602,272 B2* | 8/2003 | Boylan et al. ................ 606/200 |
| 6,626,937 B1 | 9/2003 | Cox |
| 6,638,372 B1 | 10/2003 | Abrams |
| 6,682,608 B2 | 1/2004 | Abrams et al. |
| 6,706,053 B1 | 3/2004 | Boylan et al. |
| 6,755,855 B2 | 6/2004 | Yurek et al. |
| 6,824,560 B2 | 11/2004 | Pelton |
| 7,037,320 B2* | 5/2006 | Brady et al. ................ 606/200 |
| 7,128,757 B2 | 10/2006 | Boylan et al. |
| 7,175,655 B1 | 2/2007 | Molaei |
| 7,244,319 B2 | 7/2007 | Abrams et al. |
| 7,258,753 B2 | 8/2007 | Abrams et al. |
| 2001/0007953 A1 | 7/2001 | Duerig et al. |
| 2001/0039446 A1 | 11/2001 | Edwin et al. |
| 2001/0039449 A1 | 11/2001 | Johnson et al. |
| 2001/0047202 A1 | 11/2001 | Slaikeu et al. |
| 2001/0049549 A1 | 12/2001 | Boylan et al. |
| 2002/0010481 A1 | 1/2002 | Jayaraman et al. |
| 2002/0046785 A1 | 4/2002 | Abrams et al. |
| 2002/0052627 A1* | 5/2002 | Boylan et al. ................ 606/200 |
| 2002/0062092 A1 | 5/2002 | Muni et al. |
| 2002/0068954 A1 | 6/2002 | Foster |
| 2002/0082681 A1* | 6/2002 | Boylan et al. ................ 623/1.19 |
| 2002/0087099 A1 | 7/2002 | Nanis et al. |
| 2002/0121316 A1 | 9/2002 | Abrams et al. |
| 2002/0138129 A1 | 9/2002 | Armstrong et al. |
| 2002/0193827 A1 | 12/2002 | McGuckin, Jr. et al. |
| 2003/0004536 A1* | 1/2003 | Boylan et al. ................ 606/200 |
| 2003/0036794 A1 | 2/2003 | Ragheb et al. |
| 2003/0040772 A1 | 2/2003 | Hyodoh et al. |
| 2003/0055449 A1 | 3/2003 | Lee et al. |
| 2003/0055484 A1 | 3/2003 | Lau et al. |
| 2003/0069492 A1 | 4/2003 | Abrams et al. |
| 2003/0069521 A1 | 4/2003 | Reynolds et al. |
| 2003/0120181 A1 | 6/2003 | Toma et al. |
| 2003/0127158 A1 | 7/2003 | Abrams et al. |
| 2003/0158575 A1 | 8/2003 | Boylan et al. |
| 2003/0199920 A1 | 10/2003 | Boylan et al. |
| 2003/0217794 A1* | 11/2003 | Boylan et al. ................ 148/563 |
| 2004/0084115 A1 | 5/2004 | Abrams et al. |
| 2004/0093009 A1* | 5/2004 | Denison et al. ................ 606/200 |
| 2004/0158281 A1 | 8/2004 | Boylan et al. |
| 2004/0172055 A1* | 9/2004 | Huter et al. ................ 606/200 |
| 2005/0038500 A1 | 2/2005 | Boylan et al. |
| 2006/0086440 A1 | 4/2006 | Boylan et al. |
| 2006/0212068 A1 | 9/2006 | Boylan |
| 2007/0233179 A1 | 10/2007 | Brady et al. |
| 2007/0239259 A1 | 10/2007 | Boylan |
| 2007/0249965 A1 | 10/2007 | Abrams et al. |
| 2008/0027532 A1 | 1/2008 | Boylan et al. |
| 2009/0098013 A1 | 4/2009 | Boylan et al. |
| 2009/0248130 A1 | 10/2009 | Boylan |
| 2010/0125329 A1 | 5/2010 | Lin et al. |

FOREIGN PATENT DOCUMENTS

| | | |
|---|---|---|
| EP | 0199715 | 10/1986 |
| EP | 0340304 | 11/1989 |
| EP | 0395098 | 10/1990 |
| EP | 0480427 | 4/1992 |
| EP | 0484805 | 5/1992 |
| EP | 0491349 | 6/1992 |
| EP | 0515078 | 11/1992 |
| EP | 0520073 | 12/1992 |
| EP | 0550258 | 7/1993 |
| EP | 0550288 | 7/1993 |
| EP | 0569166 | 11/1993 |
| EP | 0791340 | 8/1997 |
| EP | 0804934 | 11/1997 |
| EP | 0806220 | 11/1997 |
| EP | 0812928 | 12/1997 |
| EP | 0815803 | 1/1998 |
| EP | 0 873 734 A2 | 10/1998 |
| EP | 0879614 | 11/1998 |
| EP | 0968688 | 1/2000 |
| EP | 1027906 | 8/2000 |
| EP | 1426071 | 6/2004 |
| JP | 44-31704 | 12/1969 |
| JP | 44-32286 | 12/1969 |
| JP | 53-12759 | 2/1978 |
| JP | 55-164304 | 12/1980 |
| JP | 57-89859 | 6/1982 |
| JP | 58-161746 | 9/1983 |
| JP | 60-145155 | 7/1985 |
| JP | 60-138547 | 9/1985 |
| JP | 60-248856 | 12/1985 |
| JP | 61-84361 | 4/1986 |
| JP | 61-183455 | 8/1986 |
| JP | 62-199757 | 9/1987 |
| JP | 62-199758 | 9/1987 |
| JP | 62-235449 | 10/1987 |
| JP | 63-171570 | 7/1988 |
| JP | 64-49571 | 2/1989 |
| JP | 1-124473 | 5/1989 |
| JP | 1-242763 | 9/1989 |
| JP | 2252467 | 10/1990 |
| JP | 2289265 | 11/1990 |
| JP | 2289266 | 11/1990 |
| JP | 4-9162 | 1/1992 |
| JP | 50-19512 | 1/1993 |
| JP | 5-092044 | 4/1993 |
| JP | 6-83726 | 3/1994 |
| JP | 61-08431 | 4/1994 |
| JP | 09-215753 | 8/1997 |
| JP | 11-76420 | 3/1999 |
| JP | 2000-140124 | 5/2000 |
| JP | 03-295562 | 10/2003 |

| | | |
|---|---|---|
| JP | 4-292174 | 10/2004 |
| WO | WO 89/10088 | 11/1989 |
| WO | WO 89/12175 | 12/1989 |
| WO | WO 90/13329 | 11/1990 |
| WO | WO 91/15152 | 10/1991 |
| WO | WO 92/05828 | 4/1992 |
| WO | WO 93/19803 | 10/1993 |
| WO | WO 95/19800 | 7/1995 |
| WO | WO 97/24978 | 7/1997 |
| WO | WO 97/38747 | 10/1997 |
| WO | WO 98/20801 | 5/1998 |
| WO | WO 98/20810 | 5/1998 |
| WO | WO 99/32051 | 7/1999 |
| WO | WO 99/44542 | 9/1999 |
| WO | WO 00/04846 | 2/2000 |
| WO | WO 00/49970 | 8/2000 |
| WO | WO 00/67665 | 11/2000 |
| WO | WO 00/67668 | 11/2000 |
| WO | WO 00/69359 | 11/2000 |
| WO | WO 01/39695 | 6/2001 |
| WO | WO 01/41859 | 6/2001 |
| WO | WO 01/82830 | 11/2001 |
| WO | WO 02/36841 | 5/2002 |
| WO | WO 2002/051462 | 7/2002 |
| WO | WO 02/102281 | 12/2002 |
| WO | WO 03/002166 | 1/2003 |
| WO | WO 03/028796 | 4/2003 |
| WO | WO 03/097148 | 11/2003 |
| WO | WO 2004/033016 | 4/2004 |
| WO | WO 2004/098458 | 11/2004 |
| WO | WO 2005/102407 | 11/2005 |
| WO | WO 2006/081011 | 8/2006 |

OTHER PUBLICATIONS

U.S. Appl. No. 11/437,710, Sep. 10, 2008, Office Action.
U.S. Appl. No. 11/437,710, Apr. 6, 2010, Office Action.
U.S. Appl. No. 07/629,381, filed Dec. 18, 1990, Abrams.
U.S. Appl. No. 08/212,431, filed Mar. 11, 1994, Abrams.
U.S. Appl. No. 08/432,028, filed Mar. 1, 1995, Abrams.
U.S. Appl. No. 08/527,650, filed Sep. 13, 1995, Abrams.
U.S. Appl. No. 09/452,516, filed Dec. 1, 1999, Boylan et al.
U.S. Appl. No. 09/705,422, filed Nov. 2, 2000, Boylan et al.
U.S. Appl. No. 09/992,308, filed Nov. 13, 2001, Anderson et al.
U.S. Appl. No. 10/264,619, filed Oct. 4, 2002, Boylan et al.
U.S. Appl. No. 10/264,832, filed Oct. 4, 2002, Boylan.
U.S. Appl. No. 10/374,632, filed Feb. 25, 2003, Boylan et al.
U.S. Appl. No. 11/129,319, filed May 16, 2005, Anderson et al.
ASTM Standard No. F2004-00 "Standard Test Method for Transformation Temperature of Nickel-Titanium Alloys by Thermal Analysis" (2000).
ASTM Standard No. F2082-01 "Standard Test Method by Determination of Transformation Temperature of Nickel-Titanium Shape Memory Alloys by Bend and Free Recovery" (2001).
Barrett, R., Titanium is Tops for Implants—but Too Dear for Some, Metal Bulletin Monthly, Oct. 1999, 346, pp. 48-53(abstract only).
Boylan, John F., "The Development of Radiopaque Nitinol," Guidant Corporation, Endovascular Solutions, Temecula, CA, pp. 1-6, proceedings from "The Shape Memory and Superelastic Technologies Conference" (SMST-2003), May 5 to May 8, 2003, Asilomar Conference.
Buehler, W.J. and Cross W.B., "55-Nitinol Unique Wire Alloy with a Memory," Wire Journal, pp. 41-49 (Jun. 1969).
Cold Laser Beam Cuts Clean http://www. photonics.com/Spectra/Applications/oct02/appsCold. asp (Oct. 2002), printed Dec. 8, 2002 (2 pages).
Comparison Water jet-Laser-Microjet©, http://synova.vhosts. cogito.nimag.net/tech comparison. html, printed Dec. 8, 2002 (5 pages).
Declaration by Sepehr Fariabi, dated Sep. 16, 1993.
Duerig, T.W. et al., "An Engineer's Perspective of Pseudoelasticity," Engineering Aspect of Shape Memory Alloys pp. 369-393 (1990).
Duerig, T.W. et al., Superelastic Nitinol for Medical Devices, Medical Plastics and Biomaterials Magazine, pp. 1-14, Mar. 1997.
Duerig, T.W. et al., Ti-Ni Shape Memory Alloys, Materials Properties Handbook Titanium Alloys, *Advanced Materials*, pp. 1035-1048, ASM International (1994).
Duerig, T.W., et al., Wide Hysteresis Shape Memory Alloys, Engineering Aspects of Shape Memory Alloys, pp. 130-136 (1990).
Dueriq, T.W. et al., An Introduction to Martensite and Shape Memory, *Engineering Aspects of Shape Memory Alloys*, pp. 3-20 (1990).
Funakubo, Hirayasu Shape memory alloys, edited by, 1984, pp. v-ix, 194, 195, 204-207, 256, 257, 266-269.
*Fundamental characteristics of nickel-titanium shape memory alloy*, http://herkules.oulu.fi/isbn9514252217/html/x317.html, printed Oct. 1, 2002 (12 pages).
G.E. Dieter, Mechanical Metallurgy, 2nd edition, McGraw-Hill Book Co. pp. 204-208.
Hornbogen, E., Shape Memory: Three Usable Effects in One Material, Design Engineering, May 1990, pp. 67-73.
Hosada et al., "Phase Transformation of Ti-Ni Containing Platinum-Group Metals," Mat. Res. Soc. Symp. Proc., Materials Research Society, Vo. 753, pp. BB5.51.1-BB5.51.6 (2003).
Inoue et al., *Viscoelasticity and Morphology of Soft Polycarbonate as a Substitute for Poly(vinyl chloride)*, ICR Annual Report, 7:24-25 (2000).
Jackson C.M H.J Wagner and R.J. Wasilewski, A Report 55-Nitinol-The Alloy with a Memory: Its Physical Metallurgy, Properties, and Applications:, prepared under contract for NASA by Battelle Memorial Institute, NASA-SP5110, Technology Utilization Office National Aeronautics and Space Administration, Washington, D.C., 1972, pp. 1-2 and 19-55.
Khmelevskaya, I.Y. et al., Thermomechanical Treatment of Ti-Ni Shape memory Alloys: Transformations, Structure and Properties, *First European Conference on Shape Memory and Superelastic Technologies SMST-99*, 1-8 Sep. 5-9, 1999.
Larousse Dictionary of Science and Technology, edited by Peter Walker, 1995, p. 1056.
Lin Z.C. et al., "The Study on Superlasticity of NiTiPt wire as a Function of Application Temperature," Technical Report, Guidant Corp., pp. 1-4 (Jun. 10, 2003).
*Material properties for part design*, http://www.scudc.scu.edu/cmdoc/dg_doc/develop/material/property/a2200002.htm, printed Oct. 1, 2002 (13 pages).
Melton, Ni-Ti Based Shape memory Alloys, Engineering Aspects of Shape Memory Alloys, pp. 21-35 (1990).
Miyazaki, S. et al., Deformation and Transition Behavior Associated with the R-phase in NiTi alloys, Metallurgical Transactions A, vol. 17A, Jan. 1986, pp. 53-63.
Nishida, M. et al., Precipitation Processes in Near-Equiatomic TiNi Shape Memory Alloys, *Metallurgical Transactions* 17A, 1505-1515 (Sep. 1986).
Otsuka et al., "Shape Memory Effect," Shape Memory Materials, p. 41 (1998).
Pelton et al., "Optimisation of Processing and Properties of Medical Grade Nitinol Wire," Min. Invas. Ther. & Allied Technol. 2009(1), 107-118 (2000).
Perkins, "Ti-Ni and Ti-Ni X Shape Memory Alloys," Metal forum, vol. 3, pp. 153-163 (1981).
Poncin P., et al. "Stent Tubing: Understanding the Desired Attributes" Materials & Processes for Medical Devices Conference Sep. 8-10, 2003.
Proft et al., "The Mechanical Aspect of Constrained Recovery," Raychem Corp., pp. 115-129 (1985).
Quantities and Units of Measurement, A Dictionary and Handbook, J.V. Drazil, pp. 219, 236, and 246 (1983).
R.E. Reed-Hill, Physical Metallurgy Principals, D. Van Nostrand Co., Inc., Princeton New Jersey, pp. 231-234.
Ren et al., *Origin of rubber-like behaviour in metal alloys*, Nature, 389:579-582 (Oct. 1997).
Simon, M. et al., A Vena Cava Filter Using Thermal Shape Memory Alloy, Radiology, 125, 89-94 (Oct. 1977).
Stöckel, D. et al., Legierungen met Formgedächtnis, *Kontakt & Studium*, vol. 259, pp. 174-187 (1988) (with translation).
Stoeckel, D. et al., "Superelastic Ni-Ti Wire," Wire Journal Internation, pp. 45-50 (Mar. 1991).
Stress Strain Behavior of Polymers, http://www.eng.uc.udu/~gbeaucag/Classes/Characterization/StressStrainhtml/StressStrain. html,printed Oct. 1, 2002 (12 pages).

*The Video Extensometer*, http://www.sensorland.com/HowPage050.html., printed Dec. 8, 2002 (8 pages).

*Trade-in Program-Upgrade to NEW Instron Technology*!, http://www.instron.com/Universal testing/tradin.asp, printed Dec. 8, 2002 (2 pages).

U.S. Department of Commerce National Technical Information Service, *Effects of Alloying Upon Certain Properties of 55.1 Nitinol*, May 28, 1965.

Wayman et al., An Introduction to Martensite and Shape Memory, pp. 3-20.

Workshop on Fundamentals of Shape Memory and Workshop on Fundamentals of Shape Memory and Superelastic Alloys, (Ni-Ti Shape Memory Alloys Effects of Additions, chart only), International Organization on Shape memory and Superelastic Technologies, Asilomar, California (Mar. 6, 1994).

Yang, J.H. et al., "Stress-Induced Transformation and Superelasticity in Ni-Ti-Nb Alloys," Journal De Physique IV, pp. C8-771-C8-776 (Dec. 1995).

Zadno et al., Linear and non-linear superelasticity in Ni Ti, MRS (Materials Research Society) Int'l Meeting on Adv. Mats. vol. 9, pp. 200-206 (1989).

Zhang, C.S. et al., Pseudoelasticity of Near-Equiatomic Ni-Ti Shape Memory Alloy, *Proceedings of the First International Conference on Shape Memory and Superelastic Technologies*, pp. 383-388 (1994).

U.S. Appl. No. 07/629,381, Dec. 30, 1991, Office Action.
U.S. Appl. No. 07/629,381, Apr. 23, 1992, Office Action.
U.S. Appl. No. 07/629,381, Dec. 1, 1992, Office Action.
U.S. Appl. No. 07/994,679, Jun. 17, 1993, Office Action.
U.S. Appl. No. 07/994,679, Oct. 1, 1993, Office Action.
U.S. Appl. No. 07/994,679, Dec. 21, 1993, Notice of Allowance.
U.S. Appl. No. 08/071,322, Nov. 1, 1993, Office Action.
U.S. Appl. No. 08/071,322, Apr. 4, 1994, Office Action.
U.S. Appl. No. 08/071,322, Aug. 30, 1994, Office Action.
U.S. Appl. No. 08/071,322, Nov. 23, 1994, Notice of Allowance.
U.S. Appl. No. 08/212,431, Jan. 10, 1995, Office Action.
U.S. Appl. No. 08/212,431, Aug. 22, 1995, Notice of Allowance.
U.S. Appl. No. 08/276,082, Aug. 30, 1996, Office Action.
U.S. Appl. No. 08/276,082, Mar. 3, 1997, Office Action.
U.S. Appl. No. 08/276,082, Apr. 4, 1997, Notice of Allowance.
U.S. Appl. No. 08/432,028, Apr. 15, 1996, Office Action.
U.S. Appl. No. 08/432,028, Sep. 3, 1996, Office Action.
U.S. Appl. No. 08/484,218, May 28, 1996, Office Action.
U.S. Appl. No. 08/484,218, Sep. 16, 1996, Office Action.
U.S. Appl. No. 08/484,218, Mar. 14, 1997, Office Action.
U.S. Appl. No. 08/484,218, Dec. 1, 1997, Office Action.
U.S. Appl. No. 08/484,218, Sep. 17, 1998, Notice of Allowance.
U.S. Appl. No. 08/484,218, Sep. 7, 1999, Office Action.
U.S. Appl. No. 08/484,218, Mar. 15, 2000, Notice of Allowance.
U.S. Appl. No. 08/527,650, Dec. 11, 1995, Notice of Allowance.
U.S. Appl. No. 08/598,639, Nov. 13, 1996, Notice of Allowance.
U.S. Appl. No. 08/982,725, Feb. 25, 1999, Office Action.
U.S. Appl. No. 08/982,725, Aug. 11, 1999, Office Action.
U.S. Appl. No. 08/982,725, Feb. 28, 2000, Office Action.
U.S. Appl. No. 08/982,725, Aug. 15, 2000, Office Action.
U.S. Appl. No. 08/982,725, Jul. 18, 2001, Notice of Allowance.
U.S. Appl. No. 09/452,516, May 24, 2001, Office Action.
U.S. Appl. No. 09/452,516, Oct. 19, 2001, Office Action.
U.S. Appl. No. 09/452,516, May 20, 2002, Office Action.
U.S. Appl. No. 09/452,516, Dec. 31, 2002, Office Action.
U.S. Appl. No. 09/452,516, Apr. 11, 2003, Office Action.
U.S. Appl. No. 09/452,516, Jul. 3, 2003, Office Action.
U.S. Appl. No. 09/452,516, Jan. 13, 2004, Office Action.
U.S. Appl. No. 09/452,516, Feb. 27, 2004, Office Action.
U.S. Appl. No. 09/452,516, Apr. 22, 2004, Office Action.
U.S. Appl. No. 09/452,516, Jul. 22, 2004, Office Action.
U.S. Appl. No. 09/452,516, Jan. 18, 2005, Office Action.
U.S. Appl. No. 09/452,516, Oct. 6, 2005, Office Action.
U.S. Appl. No. 09/452,516, Mar. 13, 2006, Office Action.
U.S. Appl. No. 09/452,516, May 30, 2006, Office Action.
U.S. Appl. N. 09/452,516, Aug. 9, 2006, Office Action.
U.S. Appl. No. 09/452,516, Oct. 23, 2006, Office Action.
U.S. Appl. No. 09/452,516, Oct. 31, 2007, Office Action.
U.S. Appl. No. 09/452,516, Mar. 25, 2008, Office Action.
U.S. Appl. No. 09/452,516, Sep. 30, 2008, Office Action.
U.S. Appl. No. 09/452,516, Dec. 11, 2008, Office Action.
U.S. Appl. No. 09/452,516, Jan. 12, 2009, Office Action.
U.S. Appl. No. 09/459,814, Oct. 24, 2000, Office Action.
U.S. Appl. No. 09/459,814, Apr. 25, 2001, Office Action.
U.S. Appl. No. 09/459,814, Jul. 30, 2001, Notice of Allowance.
U.S. Appl. No. 09/498,695, Jul. 19, 2000, Office Action.
U.S. Appl. No. 09/498,695, Dec. 21, 2000, Office Action.
U.S. Appl. No. 09/498,695, Mar. 16, 2001, Notice of Allowance.
U.S. Appl. No. 09/561,747, Apr. 3, 2002, Office Action.
U.S. Appl. No. 09/561,747, Sep. 26, 2002, Office Action.
U.S. Appl. No. 09/561,747, Jan. 14, 2003, Office Action.
U.S. Appl. No. 09/561,747, Jun. 4, 2003, Office Action.
U.S. Appl. No. 09/561,747, Sep. 30, 2003, Office Action.
U.S. Appl. No. 09/561,747, Nov. 3, 2003, Notice of Allowance.
U.S. Appl. No. 09/589,592, Apr. 26, 2001, Office Action.
U.S. Appl. No. 09/589,592, Nov. 9, 2001, Office Action.
U.S. Appl. No. 09/589,592, Jan. 23, 2002, Notice of Allowance.
U.S. Appl. No. 09/589,592, May 8, 2002, Notice of Allowance.
U.S. Appl. No. 09/589,592, Aug. 7, 2002, Office Action.
U.S. Appl. No. 09/589,592, Jan. 27, 2003, Office Action.
U.S. Appl. No. 09/589,592, Jun. 4, 2003, Notice of Allowance.
U.S. Appl. No. 09/589,646, Apr. 20, 2001, Office Action.
U.S. Appl. No. 09/589,646, Feb. 13, 2002, Office Action.
U.S. Appl. No. 09/589,646, May 14, 2002, Notice of Allowance.
U.S. Appl. No. 09/589,646, Jul. 23, 2002, Notice of Allowance.
U.S. Appl. No. 09/705,422, Sep. 10, 2003, Office Action.
U.S. Appl. No. 09/705,422, Mar. 4, 2004, Office Action.
U.S. Appl. No. 09/705,422, Jul. 27, 2004, Office Action.
U.S. Appl. No. 09/705,422, Nov. 15, 2004, Office Action.
U.S. Appl. No. 09/705,422, Nov. 2, 2005, Office Action.
U.S. Appl. No. 09/705,422, Mar. 21, 2006, Office Action.
U.S. Appl. No. 09/705,422, Aug. 24, 2006, Office Action.
U.S. Appl. No. 09/705,422, Apr. 3, 2007, Office Action.
U.S. Appl. No. 09/705,422, Nov. 14, 2007, Office Action.
U.S. Appl. No. 09/705,422, Mar. 17, 2008, Office Action.
U.S. Appl. No. 09/705,422, Jan. 22, 2009, Office Action.
U.S. Appl. No. 09/705,422, Jul. 10, 2009, Office Action.
U.S. Appl. No. 09/705,422, Jan. 19, 2010, Office Action.
U.S. Appl. No. 09/752,212, Apr. 24, 2002, Office Action.
U.S. Appl. No. 09/752,212, Oct. 25, 2002, Office Action.
U.S. Appl. No. 09/752,212, Feb. 28, 2003, Office Action.
U.S. Appl. No. 09/752,212, Aug. 13, 2003, Office Action.
U.S. Appl. No. 09/752,212, Oct. 29, 2003, Office Action.
U.S. Appl. No. 09/752,212, Jan. 13, 2004, Office Action.
U.S. Appl. No. 09/752,212, Feb. 24, 2004, Office Action.
U.S. Appl. No. 09/752,212, Jun. 18, 2004, Notice of Allowance.
U.S. Appl. No. 09/882,930, Oct. 7, 2002, Office Action.
U.S. Appl. No. 09/882,930, Dec. 2, 2002, Notice of Allowance.
U.S. Appl. No. 09/884,432, Sep. 16, 2002, Office Action.
U.S. Appl. No. 09/884,432, Dec. 4, 2002, Office Action.
U.S. Appl. No. 09/884,432, Mar. 25, 2003, Notice of Allowance.
U.S. Appl. No. 09/896,435, Mar. 21, 2003, Notice of Allowance.
U.S. Appl. No. 09/992,308, Sep. 26, 2003, Office Action.
U.S. Appl. No. 09/992,308, Dec. 31, 2003, Office Action.
U.S. Appl. No. 09/992,308, Jun. 4, 2004, Office Action.
U.S. Appl. No. 09/992,308, Sep. 27, 2004, Office Action.
U.S. Appl. No. 09/992,308, Nov. 17, 2004, Office Action.
U.S. Appl. No. 10/021,528, Dec. 10, 2002, Office Action.
U.S. Appl. No. 10/021,528, Apr. 14, 2003, Notice of Allowance.
U.S. Appl. No. 10/155,910, Oct. 6, 2003, Office Action.
U.S. Appl. No. 10/155,910, May 5, 2004, Office Action.
U.S. Appl. No. 10/155,910, Aug. 23, 2004, Notice of Allowance.
U.S. Appl. No. 10/264,619, Jun. 14, 2005, Office Action.
U.S. Appl. No. 10/264,832, Jan. 10, 2005, Office Action.
U.S. Appl. No. 10/264,832, Oct. 20, 2005, Office Action.
U.S. Appl. No. 10/264,832, Jan. 13, 2006, Office Action.
U.S. Appl No. 10/264,832, Apr. 7, 2006, Office Action.
U.S. Appl. No. 10/264,832, Sep. 19, 2006, Office Action.
U.S. Appl. No. 10/291,930, Mar. 3, 2004, Office Action.
U.S. Appl. No. 10/291,930, Jun. 24, 2004, Notice of Allowance.
U.S. Appl. No. 10/291,930, Oct. 4, 2005, Office Action.
U.S. Appl. No. 10/291,930, Mar. 27, 2006, Office Action.

U.S. Appl. No. 10/291,930, Sep. 22, 2006, Office Action.
U.S. Appl. No. 10/291,930, Jan. 23, 2007, Office Action.
U.S. Appl. No. 10/299,524, Mar. 3, 2004, Office Action.
U.S. Appl. No. 10/299,524, Jun. 4, 2004, Office Action.
U.S. Appl. No. 10/327,371, Oct. 19, 2005, Office Action.
U.S. Appl. No. 10/327,371, Apr. 20, 2006, Office Action.
U.S. Appl. No. 10/327,371, Sep. 27, 2006, Office Action.
U.S. Appl. No. 10/327,371, Mar. 6, 2007, Office Action.
U.S. Appl. No. 10/327,371, May 24, 2007, Office Action.
U.S. Appl. No. 10/327,371, Oct. 9, 2007, Office Action.
U.S. Appl. No. 10/327,371, Jun. 27, 2008, Office Action.
U.S. Appl. No. 10/327,371, Nov. 26, 2008, Office Action.
U.S. Appl. No. 10/327,371, Jul. 8, 2009, Office Action.
U.S. Appl. No. 10/327.371, Apr. 15, 2010, Office Action.
U.S. Appl. No. 10/365,302, Mar. 17, 2005, Office Action.
U.S. Appl. No. 10/365,302, Oct. 4, 2005, Notice of Allowance.
U.S. Appl. No. 10/365,302, Aug. 24, 2006, Office Action.
U.S. Appl. No. 10/365,302, Mar. 29, 2007, Office Action.
U.S. Appl. No. 10/365,302, Jun. 15, 2007, Office Action.
U.S. Appl. No. 10/365,302, Dec. 12, 2007, Office Action.
U.S. Appl. No. 10/365,302, Jul. 22, 2008, Office Action.
U.S. Appl. No. 10/365,302, Dec. 9, 2008, Office Action.
U.S. Appl. No. 10/365,302, Jun. 30, 2009, Office Action.
U.S. Appl. No. 10/365,302, Jan. 15, 2010, Office Action.
U.S. Appl. No. 10/374,632, Jun. 14, 2004, Office Action.
U.S. Appl. No. 10/427,576, Dec. 23, 2009, Office Action.
U.S. Appl. No. 10/457,218, Jul. 26, 2006, Office Action.
U.S. Appl. No. 10/457,218, Nov. 22, 2006, Office Action.
U.S. Appl. No. 10/457,218, May 22, 2007, Office Action.
U.S. Appl. No. 10/457,218, Jan. 25, 2008, Office Action.
U.S. Appl. No. 10/457,218, Jul. 18, 2008, Office Action.
U.S. Appl. No. 10/457,218, Jun. 9, 2009, Office Action.
U.S. Appl. No. 10/457,218, Dec. 18, 2009, Notice of Allowance.
U.S. Appl. No. 10/457,218, Apr. 29, 2010, Notice of Allowance.
U.S. Appl. No. 10/688,401, Sep. 1, 2005, Office Action.
U.S. Appl. No. 10/688,401, Feb. 15, 2006, Office Action.
U.S. Appl. No. 10/688,401, May 19, 2006, Office Action.
U.S. Appl. No. 10/688,401, Aug. 23, 2006, Office Action.
U.S. Appl. No. 0/688,401, Dec. 18, 2006, Office Action.
U.S. Appl. No. 10/688,401, Apr. 30, 2007, Notice of Allowance.
U.S. Appl. No. 10/764,841, Oct. 17, 2006, Office Action.
U.S. Appl. No. 10/764,841, May 15, 2007, Office Action.
U.S. Appl. No. 10/764,841, Oct. 31, 2007, Office Action.
U.S. Appl. No. 10/814,326, Dec. 16, 2004, Office Action.
U.S. Appl. No. 10/814,326, Sep. 6, 2005, Office Action.
U.S. Appl. No. 10/814,326, Mar. 22, 2006, Office Action.
U.S. Appl. No. 10/900,632, Feb. 21, 2007, Office Action.
U.S. Appl. No. 10/900,632, May 7, 2007, Office Action.
U.S. Appl. No. 10/900,632, Jan. 3, 2008, Office Action.
U.S. Appl. No. 11/019,495, May 7, 2008, Office Action.
U.S. Appl. No. 11/019,495, Jan. 29, 2009, Office Action.
U.S. Appl. No. 11/019,495, Sep. 15, 2009, Office Action.
U.S. Appl. No. 11/019,495, Apr. 26, 2010, Office Action.
U.S. Appl. No. 11/437,710, Sep. 10, 2008, Office Action.
U.S. Appl. No. 11/437,710, Apr. 6, 2010, Office Action.
U.S. Appl. No. 11/723,339, Mar. 28, 2008, Office Action.
U.S. Appl. No. 11/723,339, Mar. 9, 2009, Office Action.
U.S. Appl. No. 11/723,339, Jun. 23, 2009, Office Action.
U.S. Appl. No. 11/723,339, Mar. 9, 2010, Office Action.
U.S. Appl. No. 11/783,565, Mar. 31, 2009, Office Action.
U.S. Appl. No. 11/783,565, Oct. 22, 2009, Office Action.
U.S. Appl. No. 11/870,262, Apr. 24, 2009, Office Action.
U.S. Appl. No. 11/870,262, Oct. 23, 2009, Notice of Allowance.
U.S. Appl. No. 11/870,262, Mar. 23, 2010, Notice of Allowance.
U.S. Appl. No. 11/870,262, Jul. 12, 2010, Notice of Allowance.
U.S. Appl. No. 12/369,360, Mar. 26, 2010, Office Action.
Brian L. Pelton: "Medical device having radiopacity"; U.S. Appl. No. 09/572,352, filed May 17, 2000.
Boylan et al.: "Radiopaque nitinol alloys for medical devices"; U.S. Appl. No. 09/752,212, filed Dec. 27, 2000.
Huter et al.: "Embolic filtering devices"; U.S. Appl. No. 10/377,285, filed Feb. 27, 2003.
Enami et al.: "Effect of W Addition on the Martensitic Transformation and Shape Memory Behaviour of the TiNi-Base Alloys"; Dec. 1995, pp. 629-633.
Russel et al.: "Improved NiTi Alloys for Medical Applications" 1997, pp. 429-436.
L. McDonald Schetky: "Shape Memory Alloys"; pp. 74-82.
Duerig et al.: "Engineering Aspects of Shape Memory Alloys"; 1990, pp. 369-393.
Paul G. Lindquist: "Structure and transformation behavior of martensitic Ti-(Ni, Pd) and Ti-(Ni, Pt) alloys"; University of Illinois at Urbana-Champaign, 1988.
U.S. Appl. No. 12/337,055, Aug. 16, 2010, Office Action.
Metallic materials for use with precision instruments, pp. 21-31 (Feb. 25, 1985, issued by the Nikkan Kogyo Shimbun, Ltd.).
U.S. Appl. No. 09/705,422, Oct. 25, 2010, Office Action.
U.S. Appl. No. 10/457,218, Jan. 20, 2011, Notice of Allowance.
U.S. Appl. No. 11/870,262, Nov. 15, 2010, Notice of Allowance.
U.S. Appl. No. 12/369,360, Oct. 28, 2010, Office Action.

* cited by examiner

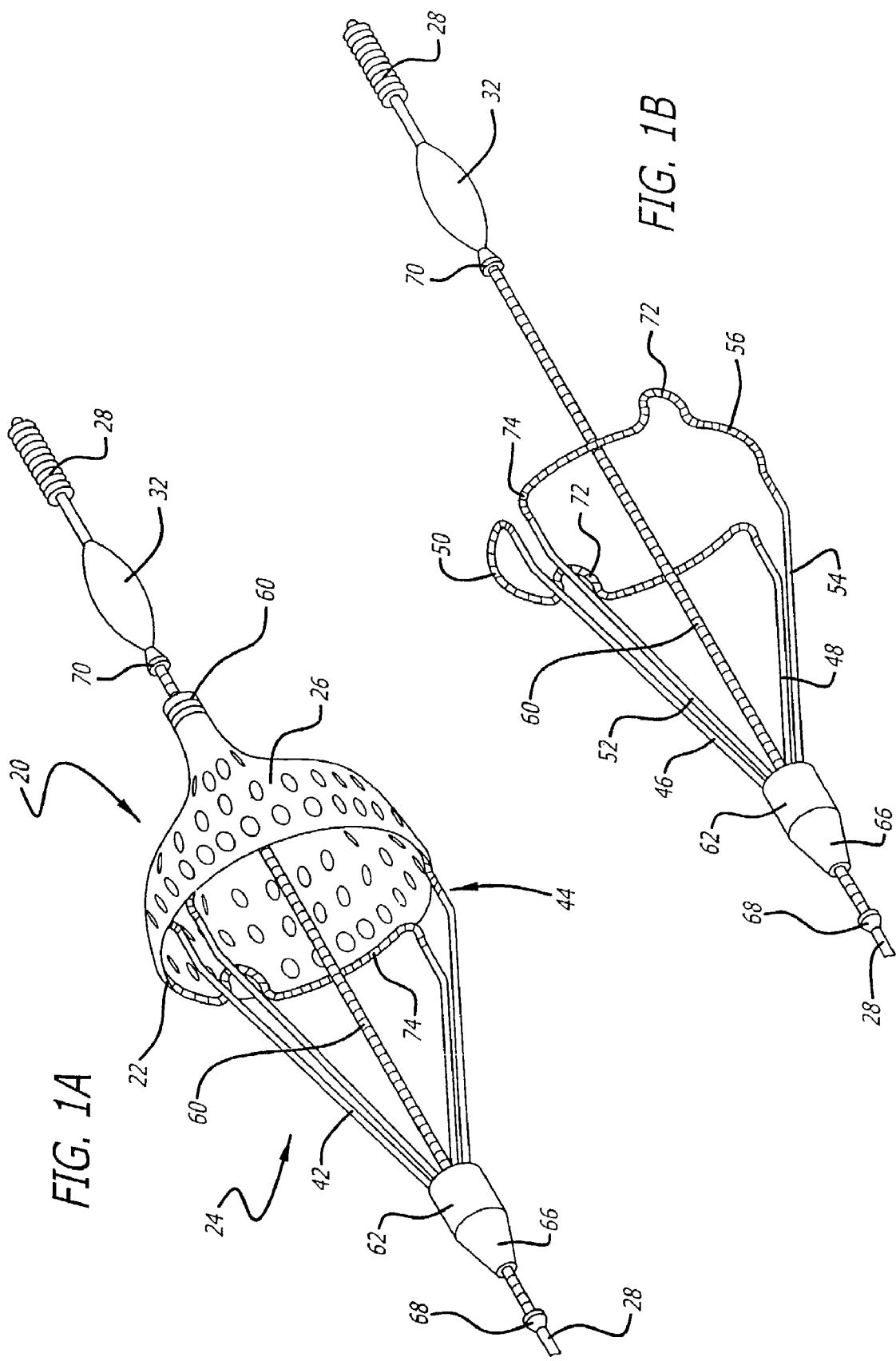

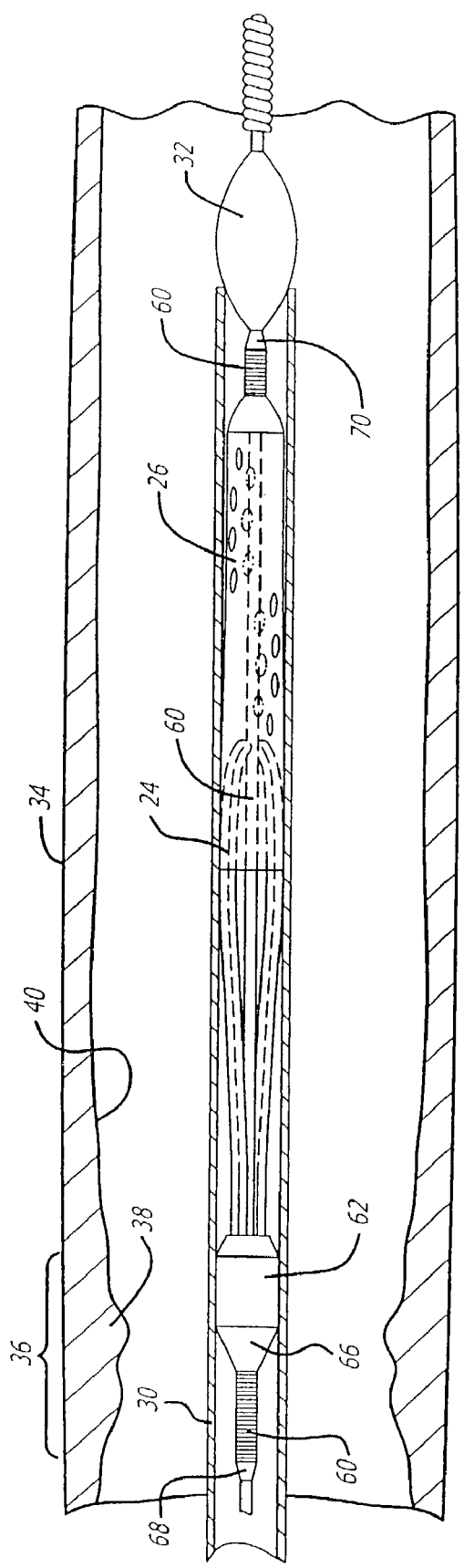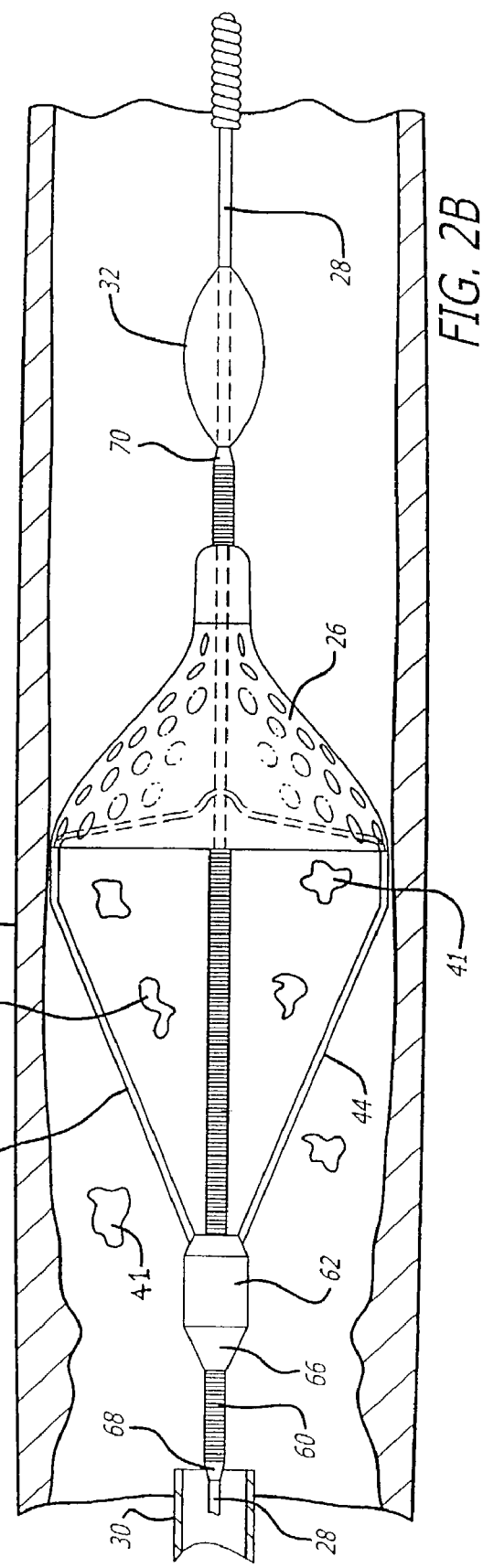

RADIOPAQUE NITINOL EMBOLIC PROTECTION FRAME

FIELD OF THE INVENTION

The present invention relates generally to filtering devices and systems which can be used, for example, when an interventional procedure is being performed in a stenosed or occluded region of a body vessel to capture embolic material that may be created and released into the body fluid during the procedure. The present invention is more particularly directed to an embolic filtering device made with a self-expanding frame (also referred to as a basket or cage) having good flexibility and bendability that is also radiopaque.

BACKGROUND OF THE INVENTION

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which uses a laser to ablate the stenosis by superheating and vaporizing the deposited plaque. Atherectomy is yet another method of treating a stenosed body vessel in which cutting blades are rotated to shave the deposited plaque from the arterial wall. A catheter is usually used to capture the shaved plaque or thrombus from the bloodstream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of frangible plaque that can travel downstream and lodge somewhere in the patient's vascular system. Pieces of plaque are sometimes generated during a balloon angioplasty procedure and released into the bloodstream. This is particularly true when the procedure is performed in a saphenous vein graft (SVG).

Additionally, while complete vaporization of plaque is the intended goal during laser angioplasty, sometimes particles are not fully vaporized and enter the bloodstream. Likewise, not all of the emboli created during an atherectomy procedure may be drawn into the catheter and, as a result, enter the bloodstream.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to address the problem created when debris or fragments enter the circulatory system following vessel treatment using any one of the above-identified procedures. One approach is to cut the debris into minute sizes which pose little chance of becoming occluded in major vessels within the patient's vasculature. However, it is often difficult to control the size of the fragments that are formed. So the potential risk of vessel occlusion still exists, making such a procedure in the carotid arteries a high-risk proposition.

Other techniques include the use of catheters with a vacuum source that provides temporary suction to remove embolic debris from the bloodstream. On the other hand, there can be complications associated with such systems if the vacuum catheter does not remove all of the embolic material from the bloodstream. Also, a powerful suction could cause trauma to the patient's vasculature.

Another technique which has had some success deploys a filter or trap downstream from the treatment site to capture embolic debris before they reach the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self-expanding and rely on a restraining sheath that maintains the expandable filter in the collapsed position until it is ready to be expanded at the target site within the patient's vasculature. At the target site, the physician retracts the proximal end of the restraining sheath to expose the expandable filter, allowing the filter to self-expand at the desired location. Once the procedure is completed, the filter can be collapsed. The filter with the trapped embolic debris can then be removed from the vessel.

While a filter can be effective in capturing embolic material, the filter still needs to be collapsed and removed from the vessel. During these steps, there is a possibility that trapped embolic debris can backflow through the inlet opening of the filter and re-enter the bloodstream. Therefore, it is important that any captured embolic debris remain trapped within the filter so that particles are not inadvertently released back into the body vessel.

Some prior art expandable filters are attached to the distal end of a guide wire or guide wire-like member which allows the filtering device to be steered in the patient's vasculature as the guide wire is positioned by the physician. Once the guide wire is in proper position in the vasculature, the embolic filter is deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath is delivered over the guide wire using over-the-wire techniques to collapse the expanded filter for removal from the patient's vasculature.

When a combination of an expandable filter and a guide wire is used, the expandable filter portion should be flexible in order to negotiate the often tortuous anatomy through which it is being delivered. An expandable filter that is too stiff could prevent the device from reaching the desired deployment position within the patient's vasculature. As a result, there is a need to increase the flexibility of the expandable filter without compromising its structural integrity once in position within the patient's body vessel. Also, while it is beneficial if the area of treatment is located in a substantially straight portion of the patient's vasculature, sometimes the area of treatment is at a curved portion of the body vessel which can be problematic to the physician when deploying the expandable filter. If the expandable filter portion is too stiff, it is possible that the filter may not fully deploy within the curved portion of the body vessel. As a result, gaps between the filter and vessel wall can form that may permit some embolic debris to pass therethrough. Therefore, the filtering device should be sufficiently flexible to be deployed in, and to conform to, a tortuous section of the patient's vasculature when needed.

Expandable filters can be provided with some increased flexibility by forming the struts of the filter assembly from relatively thin material. The use of thin material, however, often reduces the radiopacity of the expandable filter. This often makes it difficult for the physician to visualize the filter during deployment. Conversely, the use of thicker materials, which can promote radiopacity of the expandable filter, usually reduces its flexibility and may impair the deliverability of the expandable filter within the patient.

In addition, nickel-titanium alloys have been used to make embolic filters. But visualization of filters made from a nickel-titanium alloy, which has relatively low radiopacity as compared to other metallic materials, is also difficult during fluoroscopy.

What has been needed is an expandable filter assembly having high flexibility with sufficient strength and radiopacity to be successfully deployed within a patient's vasculature to collect embolic debris. The present invention disclosed herein satisfies these and other needs.

SUMMARY OF THE INVENTION

The present invention provides a flexible self-expanding frame for use with an embolic filtering device designed to capture embolic debris created during the performance of a therapeutic interventional procedure, such as a balloon angioplasty or stenting procedure, in a body lumen. The present invention provides the physician with an embolic filtering device having the flexibility needed to be steered through tortuous anatomy, yet possessing sufficient strength to hold open a filtering element against the wall of the body lumen for trapping embolic debris. Also, the present invention provides sufficient flexibility without compromising the radiopacity characteristics of the filtering device. Thus, an embolic filtering device made in accordance with the present invention is radiopaque, relatively easy to deploy, and has good flexibility and conformability to the patient's anatomy.

In one embodiment, an embolic filter assembly of the present invention includes an expandable frame made from a self-expanding material, preferably, linear pseudoelastic nickel-titanium (NiTi or nitinol). The frame may be made from a pair of half frames capable of expanding from an unexpanded position having a first delivery diameter to an expanded or deployed position having a second expanded diameter. A filter element made from an embolic-capturing material is attached to the expandable frame to move between the unexpanded position and deployed position.

The half frames which cooperatively form the expandable frame can be set to remain in the expanded, deployed position until an external force is placed over the half frames to collapse and move the frames to the unexpanded position. One way of accomplishing this is through the use of a restraining sheath, for example, which can be placed over the filtering device in a coaxial fashion to contact the half frames and move the half frames into the unexpanded position.

The embolic filtering device can be attached to the distal end of an elongated member, such as a guide wire, for temporary placement in the vasculature. A guide wire may be used in conjunction with the filtering device when embolic debris is to be filtered during, for example, an interventional procedure. In this manner, the guide wire and filtering assembly, with the restraining sheath placed over the filter assembly, are introduced into the patient's vasculature. Once the physician manipulates the guide wire into the target area, the restraining sheath is retracted to deploy the expandable frame into the expanded position. This can be easily performed by the physician by simply retracting the proximal end of the restraining sheath located outside of the patient. Once the restraining sheath is retracted, the self-expanding properties of the frame cause each half frame to move in an outward, radial fashion away from the guide wire to contact the wall of the body vessel. As the half frames expand radially, so does the filter element, which is now maintained in place to collect embolic debris that may be released into the bloodstream as the physician performs the interventional procedure. The guide wire is also used by the physician to deliver the necessary interventional device into the area of treatment.

The present invention contemplates an embolic filter frame made from a linear pseudoelastic alloy. The alloy is preferably nickel-titanium, also known as Ni—Ti or nitinol. The linear pseudoelastic properties of the nitinol exploit a shape setting capability without eventually developing stress-induced martensite. This is accomplished by cold forming the alloy to achieve its intended shape, with optional, limited heat treatment so no stress plateau appears in the stress-strain curve of the alloy. Indeed, while positioned inside the body lumen, the embolic filter frame is in the martensitic phase only, and does not undergo a phase change when stressed.

In addition, the nickel-titanium material used in one embodiment of the present invention frame is alloyed with a ternary element selected from the group of elements consisting of iridium, platinum, gold, rhenium, tungsten, palladium, rhodium, tantalum, silver, ruthenium, or hafnium. Addition of one or more of these elements to the binary nickel-titanium alloy enables the frame to become radiopaque. That is, the nickel-titanium alloyed with the ternary element produces a frame that is appreciably more radiopaque that an identical frame made only from binary nickel-titanium.

The addition of the ternary element improves radiopacity yet does not detract from the engineering qualities of the nickel-titanium alloy. To be sure, the linear pseudoelasticity aspect of the nitinol with the ternary element addition remains a highly elastic metal as compared to steel.

The present invention is particularly useful when an interventional procedure, such as balloon angioplasty, stenting procedure, laser angioplasty or atherectomy, is being performed in a critical body lumen such as the carotid arteries where the release of embolic debris into the bloodstream can occlude the flow of oxygenated blood to the brain, resulting in grave consequences to the patient. While the present invention is particularly useful in carotid procedures, the invention can be used in conjunction with any vascular procedure in which embolic risk is present.

The present invention can be used in arteries, veins, and other body vessels. It is to be understood that the present invention is not limited by the embodiments described herein. Other features and advantages of the present invention will become more apparent from the following detailed description of the invention when taken in conjunction with the accompanying exemplary drawings.

BRIEF DESCRIPTION OF THE DRAWINGS

FIG. 1A is a perspective view of an embolic filtering device embodying features of the present invention.

FIG. 1B is a perspective view of the embolic filtering device of FIG. 1A shown without the filter element attached to the expandable frame.

FIG. 2A is a side elevational view, partially in cross-section, of the embolic filtering system shown in FIG. 1C as it is being delivered within a body lumen.

FIG. 2B is a side elevational view, partially in cross-section, similar to that shown in FIG. 2A, wherein the embolic filtering device is deployed in its expanded position within the body vessel.

DETAILED DESCRIPTION OF THE PREFERRED EMBODIMENTS

Figure 1C:
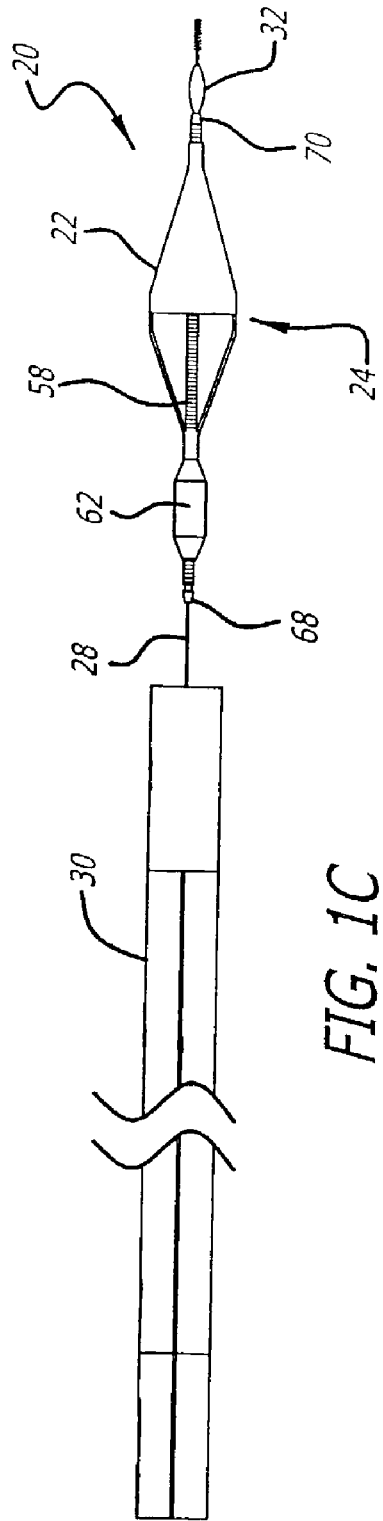
FIG. 1C is a side elevational view of an embolic filtering system which includes the embolic filtering device of FIG. 1A and a delivery sheath.

Turning now to the drawings, in which like reference numerals represent like or corresponding elements in the drawings, FIGS. 1A, 1B and 1C illustrate one particular embodiment of an embolic filtering device 20 incorporating features of the present invention. This embolic filtering device 20 is designed to capture embolic debris which may be created and released into a body vessel during, for example, an interventional procedure. The embolic filtering device 20 includes an expandable filter assembly 22 having a self-expanding frame 24 (also referred to as a basket) and a filter element 26 attached thereto. In this particular embodiment, the expandable filter assembly 22 is rotatably mounted near the distal end of an elongated tubular or solid support shaft, such as a steerable guide wire 28. A restraining or delivery sheath 30 (see FIGS. 1C and 2A) extends coaxially along the guide wire 28 in order to maintain the expandable filter assembly 22 in its unexpanded, delivery position until it is ready to be deployed within the patient's vasculature.

The expandable filter assembly 22 can be deployed by the physician by simply retracting the restraining sheath 30 proximally to expose the expandable filter assembly. Once the restraining sheath is retracted, the self-expanding wire frame 24 becomes uncovered and immediately begins to expand within the body vessel (see FIGS. 2A and 2B), causing the filter element 26 to move into a deployed position.

An optional obturator 32 is affixed to the guide wire 28 distal to the filter assembly 22 to prevent possible "snowplowing" of the embolic filtering device as it is being delivered through the vasculature. The obturator 32 can be made from a soft polymeric material, such as PEBAX 40D, and preferably has a smooth surface to help the embolic filtering device 20 travel through the body vessels and cross lesions while preventing the distal end of the restraining sheath 30 from "digging" or "snowplowing" into the wall of the body vessel. The end of the delivery sheath 30 preferably partially extends over the obturator 32 (FIG. 2A) so that a smooth outer surface is created between these components.

In FIGS. 2A and 2B, the embolic filtering device 20 is shown as it is being delivered within an artery 34 or other body vessel of the patient. Referring specifically now to FIG. 2B, the embolic filtering assembly 22 is shown in its expanded position within the patient's artery 34. This portion of the artery 34 has an area of treatment 36 (FIG. 2A) in which atherosclerotic plaque 38 has built up against the inside wall 40 of the artery 34. The filter assembly 22 can be placed distal to, and downstream from, the area of treatment 36. For example, the therapeutic interventional procedure may comprise the implantation of a stent (not shown) to increase the diameter of an occluded artery and increase the flow of blood therethrough.

The expandable frame 24 preferably includes a pair of half frames 42 and 44 (also referred to as D-frames) which, upon release from the restraining sheath 30, expand the filter element 26 into its deployed position within the artery (FIG. 2B). Embolic debris created during the interventional procedure and released into the body fluid is captured within the deployed filter element 26. Although not shown, a balloon angioplasty catheter could be initially introduced within the patient's vasculature in a conventional Seldinger technique through a guiding catheter. The guide wire 28 is disposed through the area of treatment and the dilatation catheter can be advanced over the guide wire 28 within the artery 34 until the balloon portion is directly in the area of treatment 36. The balloon of the dilatation catheter is inflated, expanding the plaque 38 against the wall 40 of the artery 34 thus opening the artery and reducing the occlusion in the vessel at the position of the plaque 38.

After the dilatation catheter is removed from the patient's vasculature, a stent (not shown) can be implanted in the area of treatment 36 using over-the-wire or rapid exchange techniques to help hold and maintain the patency of this portion of the artery 34. The stent also helps prevent restenosis from developing in the area of treatment. The stent could be delivered to the area of treatment on a stent delivery catheter (not shown) which is advanced from the proximal end of the guide wire to the area of treatment. Any embolic debris 41 created during this interventional procedure will be released into the bloodstream and will enter the filter element 26. Once the procedure is completed, the interventional device may be removed from the guide wire. The filter assembly 22 thereafter can be collapsed and removed from the artery 34, taking with it any embolic debris trapped within the filter element 26. A recovery sheath (not shown) can be delivered over the guide wire 28 to collapse the filter assembly 22 for removal from the patient's vasculature.

As seen in FIGS. 1A-1E, the frame 24 preferably includes a first half frame 42 and second half frame 44 that cooperatively form a deployment mechanism for expanding the filter element 26 within the patient's vasculature. The first half frame 42 includes a first control arm 46 and a second control arm 48 connected to each other via a partial loop 50 which extends radially outward once placed in the deployed position as is shown in FIG. 1B. Likewise, the second half frame 44 includes a first control arm 52 and a second control arm 54 connected by a partial loop 56. These partial loops form a D-shaped structure when placed in an expanded position. Once placed in the deployed position, as is shown in FIG. 1B, the partial loops 50 and 56 cooperatively form a composite circular shaped loop having a large opening to which the filter element 26 is attached. In this fashion, once the first half frame 42 and the second half frame 44 are deployed, the partial loops 50 and 56 will self-expand radially to contact the wall of the artery to maintain proper wall apposition to prevent gaps from forming between the filer element 26 and the wall of the body vessel. Again, these half frames are sometimes referred to as D-frames since the partial loops form a D-shaped once deployed. Any embolic debris or unwanted particles which may be entrained in the body fluid passing through the body vessel should be captured in the filter element 26.

The filtering assembly 22 is optionally rotatably mounted onto the guide wire 28 via a filter support structure 58. This filter support structure 58 is preferably a filter coil 60, and provides a suitable amount of flexibility and bendability to the composite filter assembly as the device is being delivered through the sometimes tortuous paths leading to the area of treatment. As can be seen in FIGS. 1A and 1B, this filter coil 60 can extend from a position proximal to the frame 24 to a position distal to the end of the filter element 26. While a wire coil is employed as the filter coil 60, it should be appreciated by those skilled in the art that other structures may be used. For example, a piece of tubing made from a polymeric material or a nickel-titanium hypotube having good flexibility also could be used as the filter support structure. Another suitable material for the filter coil is 304 stainless steel spring wire having a diameter of about 0.002 to ±0.0002 inch.

Figure 1E:
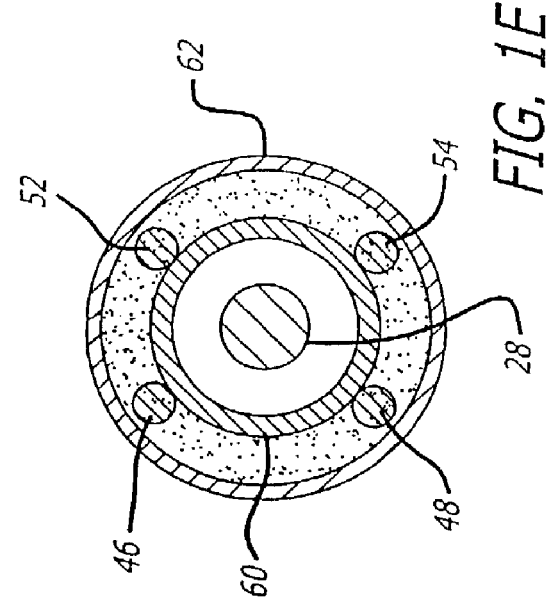
FIG. 1E is a cross-sectional view taken along line 1E-1E from FIG. 1D.
Figure 1D:
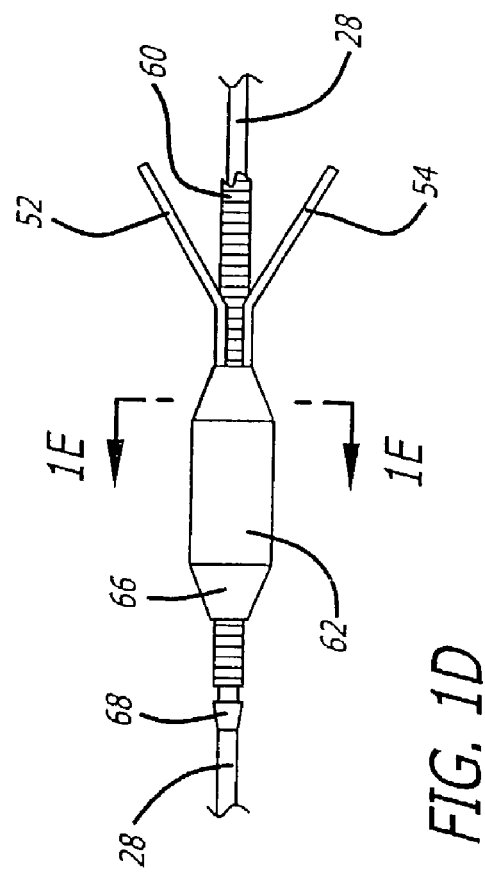
FIG. 1D is a side elevational view of the proximal end of the embolic filtering device of FIG. 1A showing in greater detail a pair of half frames mounted to the filter coil.

As can best be seen in FIGS. 1A-1C, each of the first and second control arms of the first half frame 42 and the second half frame 44 are connected at a sleeve or collar 62 located proximal to the partial loops 50 and 56. In this regard, the ends of each of the first and second control arms are connected substantially together by this collar 62. This collar 62 can be mounted over the ends of the first and second half frames to maintain the ends fixedly disposed between the collar 62 and the filter coil 60. This collar 62 can be made from a highly radiopaque material such as a platinum/iridium alloy having a material composition of 90% platinum and 10% iridium. More specifically, FIGS. 1D and 1E show one particular arrangement for mounting the half frames to the filter coil 20. Solder 66 is placed over the ends of the first and second half frames in order to create a smooth, tapered surface with the outer surface of the collar 62. A tapered solder joint 66 located proximal to the collar 62 also can be utilized to help maintain the first and second half frames mounted onto the filter coil 60. This solder joint 66 also provides a smooth taper with the outer surface of the collar 62. It will be appreciated by those skilled in the art that still other ways of mounting the first and second half frames onto the filter support structure 58 can be implemented in accordance with the present invention.

As can best be seen in FIGS. 1A-1C, the filter assembly 22 is disposed between a proximal stop fitting 68 and distal stop fitting 70 placed on the guide wire 28. In this manner, the stop fittings 68 and 70 abut against the ends of the filter coil 60 to either inhibit longitudinal motion of the filter assembly 22 relative to the guide wire 28 completely or to provide a limited range of motion along the guide wire 28. As is shown in the same figures, the proximal fitting 68 and distal fitting 70 are placed in close proximity to the ends of the filter coil 60 to prevent any appreciable amount of longitudinal motion of the filter assembly 22 relative to the guide wire 28. However, the spacing between the proximal fitting 68 and distal fitting 70 can be increased to allow a limited range of motion of the filter assembly relative to the guide wire. Additionally, this particular mounting system allows the filter assembly 22 to be rotatably mounted onto the guide wire 28 to permit the guide wire 28 to rotate freely once the first and second half frames 42 and 44 are deployed in the body vessel. In this manner, if the physician should spin the guide wire at its proximal end while placing an interventional device on the guide wire, that rotation will not be transmitted along the guide wire to the deployed wire frame 24. Thus, the frame 24 and the filter element 26 should remain stationary in the event of accidental or intentional rotation of the guide wire at its proximal end.

Referring now to FIG. 2A, the first half frame 42 and second half frame 44 are shown in a collapsed, delivery position within the restraining sheath 30. As can be seen in FIG. 2A, the first and second control arms and partial loop forming the half frames actually define a single, complete loop which extends in a longitudinal fashion within the restraining sheath 30. In order to release the crossing profile of the restraining sheath 30, the control arms should be brought together as close as possible when collapsed. Once the restraining sheath 30 has been retracted, the self-expanding properties of the material used to manufacture the first and second half frames 42 and 44 allow the partial loops to radially expand outward to the deployed position shown in FIG. 2B. The control arms will expand radially outward to some degree as well. Once deployed, the partial loops 50 and 56 cooperatively form a complete circular loop which forms an opening for the filter element 26.

In order to maintain a small crossing profile, the delivery sheath 30 should have a small diameter to create the small crossing profile, yet must be large enough to house the collapsed filtering assembly 22 therein. As can be seen in FIG. 2A, each of the half frames must be sufficiently collapsed in order to fit within the lumen of the delivery sheath 30. In order to assist in reaching this collapsed position, it may be beneficial to create a flex region 72 on each of the partial loops 50 and 56 of the first and second half frames. This flex region 72 can be formed, as is best shown in FIG. 1B, as a D-shaped bend region located at the apex or near the apex of each of the partial loops. This flex region 72 helps to collapse the half frame into the sheath 30. The optional addition of this flex region 72 at the apex of the partial loop also increases the surface area for improved distribution of the expansional force exerted by the device to the interior wall of a body vessel once deployed. It also improves the radiopaque image created by the device during fluoroscopy.

As can be seen in FIG. 1B, this flex region 72 extends from the substantial D-shape of the expanded loop portion and is substantially parallel with a linear axis defined by the guide wire. In this regard, the flex region extends distally away from the partial loop and is almost perpendicular to the linear axis defined by the expanded partial loop. In the particular embodiment shown in FIG. 1B, the flex region 72 has a D-shape that is located near or at the apex of the expanded partial loops 50, 56. The D-shape of the flex region 72 enables the half frame to more easily collapse to its delivery position within the delivery sheath since the partial loop now is preformed with a working "hinge" that allows the control arms to more easily collapse closer to each other.

The D-shaped partial loops 50, 56 in this embodiment also include an optional radiopaque wire coil 74 that wraps around each partial loop to enhance the radiopacity of the device under fluoroscopy. Since nickel-titanium is used in some embodiments to create the frame 24 of the present invention, there may be a desire to increase the radiopacity of the device under fluoroscopy. Hence, a very small diameter wire 74 is wrapped around the partial loops forming the half frames to increase visualization of the device during fluoroscopy. One suitable material for this radiopaque wire is gold-plated tungsten wire having about 5-7% gold plating. The wire can have a diameter of about 0.0010±0.0002 inch, although the diameter can vary depending on the size of the expandable frame 24. It should be appreciated that other radiopaque markers and marking systems known in the art may be added to the filter assembly 22 in order to enhance visibility during fluoroscopy.

Although the various embodiments of the embolic filtering apparatus have been shown as being mounted between fittings attached to a guide wire, the embodiments shown can be also deployed in an over-the-wire fashion as well. The steerable guide wire can be first initially steered into the target location by the physician. Thereafter, the embolic filtering assembly, which includes the expandable frame and filter element, can then be delivered to the target area in an over-the-wire fashion via the guide wire. The delivery sheath can extend over the embolic filtering assembly and be moved with the filter assembly over the guide wire to the distal end of the guide wire, where the filter assembly can then be deployed. Using this technique, it may be easier to first steer the guide wire into the target area and thereafter deliver the filtering assembly into the target area using an over-the-wire technique. It should be appreciated that a fitting may be required on the guide wire to hold and maintain the filtering assembly to the wire once the filtering assembly has been delivered to the distal end section of the guide wire. Alternatively, the filter coil used in conjunction with the filter assembly may be connected with the distal coil wire of the guide wire as a means for holding the filter assembly in place. The filter coil could have a coil which is wound opposite the coil of the guide wire to allow some intermeshing of the components in order to maintain the filtering assembly stationary on the guide wire. Thereafter, once the interventional procedure has been performed, a recovery sheath recovers the filter assembly.

The expandable frames of the present invention can be made in many ways. One way is to use a single wire made from a material possessing highly elastic or shape memory properties. The wire can be fashioned then preset to deploy into a desired three-dimensional size and shape. The deployment would be triggered by the material's elasticity or shape memory.

Another method of making the frame is to cut a tubular-shape pattern from a self-expanding material, such as nickel-titanium. The cutting process removes portions of the tubing in the desired pattern for each half frame or full frame, leaving relatively untouched the portions of the tubing that are to form the control arms and partial loop(s). The tubing may be cut into the desired pattern by means of a machine-controlled laser. Prior to laser cutting the pattern, the tubular member could be formed with varying wall thicknesses which can be used to create flexing portions on the half frames. The frame can also be fashioned from braided filaments similar in construction to rope.

The tubing, wire, or filaments used to make the frames may be made of biocompatible material such as nickel-titanium, spring steel, or the like. Elgiloy is another material which could possibly be used to fabricate the frames. Also, highly elastic polymers can be used to form the frames.

The filter size is often very small, so the wire, tubing, or braid from which the half frames are made must necessarily have a small diameter. Typically, the tubing has an outer diameter on the order of about 0.020-0.5 inch in the deployed condition. The wall thickness of the tubing is usually about 0.076 mm (0.003-0.006 inch). The diameter of a wire that can be used to form the expandable frame can be as small as about 0.0036 inch. Of course, large diameter wire could be used as well. When multiple stranded or braided wire is used, the diameter of the composite wire can be about 0.006 inch. As can be appreciated, the width and/or thickness at the strain distributing strut is smaller preferably. For frames implanted in body lumens, such as PTA applications, the dimensions of the tubing may be correspondingly larger.

Generally, when the frame or half frame is laser cut, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished frame. The frame can be laser cut much like a stent is laser cut. Details on how a tubing can be cut by a laser are found in, for example, U.S. Pat. No. 5,759,192 (Saunders), U.S. Pat. No. 5,780,807 (Saunders) and U.S. Pat. No. 6,131,266 (Saunders), which have been assigned to Advanced Cardiovascular Systems, Inc.

In general, the process of cutting a pattern for the frame out of the tubing is automated except for loading and unloading the length of tubing. For example, a pattern can be cut in tubing using a CNC-opposing collet fixture for axial rotation of the length of tubing in conjunction with CNC X/Y table to move the length of tubing axially relative to a machine-controlled laser as described. The entire space between collets can be patterned using the CO2 or Nd:YAG laser set-up. The program for control of the apparatus is dependent on the particular configuration desired and the pattern to be ablated in the coding.

In one example, the frame of the present invention can be laser cut from a tube of nickel-titanium whose transformation temperature is below body temperature. After the pattern of each frame is cut into the hypotube, the tubing is expanded and heat treated to be stable at the desired final diameter. Alternatively, the frames can be made from nitinol wire with the shape of the frames being set via techniques known in the art. The heat treatment also can control the transformation temperature of the frame such that it is superelastic at body temperature if so desired.

The frame is made to an expanded diameter size that is larger than the inside diameter of the target vessel. In this way the self-expanding control arms apply an outward radial force to the vessel wall. The nickel-titanium can be processed so that it exhibits non-linear pseudoelasticity (i.e., superelasticity) and self-expands upon deployment as described above. Specifically, the frame is heat set to self-expand to this larger diameter.

The present invention frame remains in its open position while at body temperature and can be manipulated into its unexpanded position upon application of a low temperature. One method allows the frame to undergo a phase change which would facilitate the frame and filter element being inserted into the restraining sheath. Lowering the temperature is accomplished by chilling the filter assembly in a cooling chamber maintained at a temperature preferably below the martensite finish temperature by exposure to liquid nitrogen. Once the frame, or more precisely, the control arms, are manipulated into their collapsed state, the restraining sheath can be placed over the frame to prevent the arms from expanding once the temperature is brought up to room temperature, which is usually above the austenite start temperature ($A_s$).

Alternatively, the present invention frame is fabricated by laser cutting a large diameter tubing of nickel-titanium. The large diameter tubing creates a frame already in its expanded state. The frame is manipulated into its unexpanded position by squeezing and then backloading the frame into a restraining sheath, which keeps the frame in the unexpanded position until it is ready for use. If the frame is formed in this manner, there is no need to heat set the tubing to the final expanded diameter. This process of forming the frame can be applied to either superelastic or shape-memory nickel-titanium.

The present invention further seeks to preserve the engineering qualities of nickel-titanium alloys just described above yet improve upon the material's radiopacity by addition of a ternary element. This is preferably accomplished in one embodiment by forming a composition consisting essentially of about 30 to about 52 atomic percent titanium and the balance nickel and up to 10 percent of one or more additional ternary alloying elements. Such ternary alloying elements may be selected from the group consisting of iridium, platinum, gold, rhenium, tungsten, palladium, rhodium, tantalum, silver, ruthenium, or hafnium. In the preferred embodiment, the atomic percentage of platinum is greater than or equal to 2.5 and less than or equal to 15. In an alternative embodiment, the atomic percentage of palladium is greater than or equal to 2.5 and less than or equal to 20.

A preferred embodiment frame according to the present invention is made from an alloy having approximately 42.8 atomic percent nickel, 49.7 atomic percent titanium, and 7.5 atomic percent platinum. Through empirical studies, the aforementioned compositions produce a tubular structure having a radiopacity comparable to the same size and pattern of a tubular structure made from 316 L stainless steel with a 2.7 to 6.5 μm gold coating.

In various alternative embodiments, the present invention contemplates the minor addition of a quaternary element, for example, iron, to further enhance the alloy's formability or its thermomechanical properties. The presence of impurities such as carbon or oxygen or the like in the present invention alloy is also possible.

A preferred method of fabricating the present invention linear pseudoelastic, radiopaque metallic frame entails first fashioning nickel-titanium tubing. Similar steps may be used to fashion wire as well. In this example, the tubing is made from vacuum induction melting nickel and titanium with the ternary element according to the compositions suggested above. The ingot is then remelted for consistency. The ingot is next hot rolled into bar stock, then straightened and sized, and hot or cold formed into a cylinder. The cylinder is gun drilled to form the tubing. Instead of gun drilling, other methods of material removal known in the art may be used, including electric discharge machining (EDM), laser beam machining, and the like. Next, the tubing is cold drawn and annealed repeatedly to achieve the finished dimensions. The final reduction sequence should be between 20 to 50 percent cold work followed by no subsequent heat treatment. The cold drawing process involves reducing the diameter by drawing through a sequence of smaller diameter dies. The tube reduction process may include a mandrel over which the tube can be drawn. Of course, those skilled in the art understand that other methods of cold drawing small diameter tubing can be employed.

The following are additional processing guide posts for the present invention to achieve a sufficiently radiopaque frame yet maintaining the engineering stress-strain characteristics of the alloy. Empirical evidence suggests that, in various preferred embodiments, a Ni—Ti—Pd or Ni—Ti—Pt ingot should have the following austenite finish temperature: 0 degrees C.$\leq A_f \leq$40 degrees C. The Ni—Ti—Pd or Ni—Ti—Pt tubing or wire should exhibit an austenite finish temperature of: −15 degrees C.$\leq A_f \leq$15 degrees C. In an exemplary embodiment, the final laser cut Ni—Ti—Pd or Ni—Ti—Pt frame should exhibit an austenite finish temperature of: 0 degrees C.$\leq A_f \leq$37 degrees C. Of course, the $A_f$ of the finished laser cut frame can be set as needed by limited heat treating processes known in the art.

It is understood that the austenite finish temperature ($A_f$) is defined to mean the temperature at which the material completely reverts to austenite. In technical terms, the $A_f$ (and other transformation temperatures $A_s$, $M_s$, $M_f$) as it applies to an ingot made of Ni—Ti—Pd or Ni—Ti—Pt, for example, is determined by a Differential Scanning Calorimeter (DSC) test, known in the art. The DSC test method to determine transformation temperatures for the ingot is guided by ASTM standard no. F 2004-00, titled "Standard Test Method For Transformation Temperature Of Nickel-Titanium Alloys By Thermal Analysis."

The "active $A_f$" for the tubing or wire and the finished device is determined by a bend and free recovery test, also known in the art. In such a test, the tubing or wire is cooled to under the $M_f$ temperature, deformed, and warmed up. While monitoring the increasing temperature, the point of final recovery of the deformation in the tubing approximates the $A_f$ of the material. The active $A_f$ testing technique is guided by a second ASTM standard titled "Standard Test Method For Determination Of Transformation Temperature Of Nickel-Titanium Shape Memory Alloys By Bend And Free Recovery," or by equivalent test methods known in the art.

Samples of wire made in accordance with the foregoing exemplary embodiments were tested. Specifically, the stress-strain relationship based on empirical data for nickel-titanium-palladium and nickel-titanium-platinum are plotted against binary nitinol in FIG. 3. Curve A corresponds to a sample of nickel-titanium-platinum. Curve B is based on a sample of binary nitinol. Curve C is based on a sample of nickel-titanium-palladium. To generate the empirical data, the wire samples were placed under increasing tension until past the phase transformation from their initial austenitic phase to their martensitic phase. Tension was then slowly released prior to any plastic deformation until stress on the samples dropped to zero with full deformation recovery.

Figure 3:
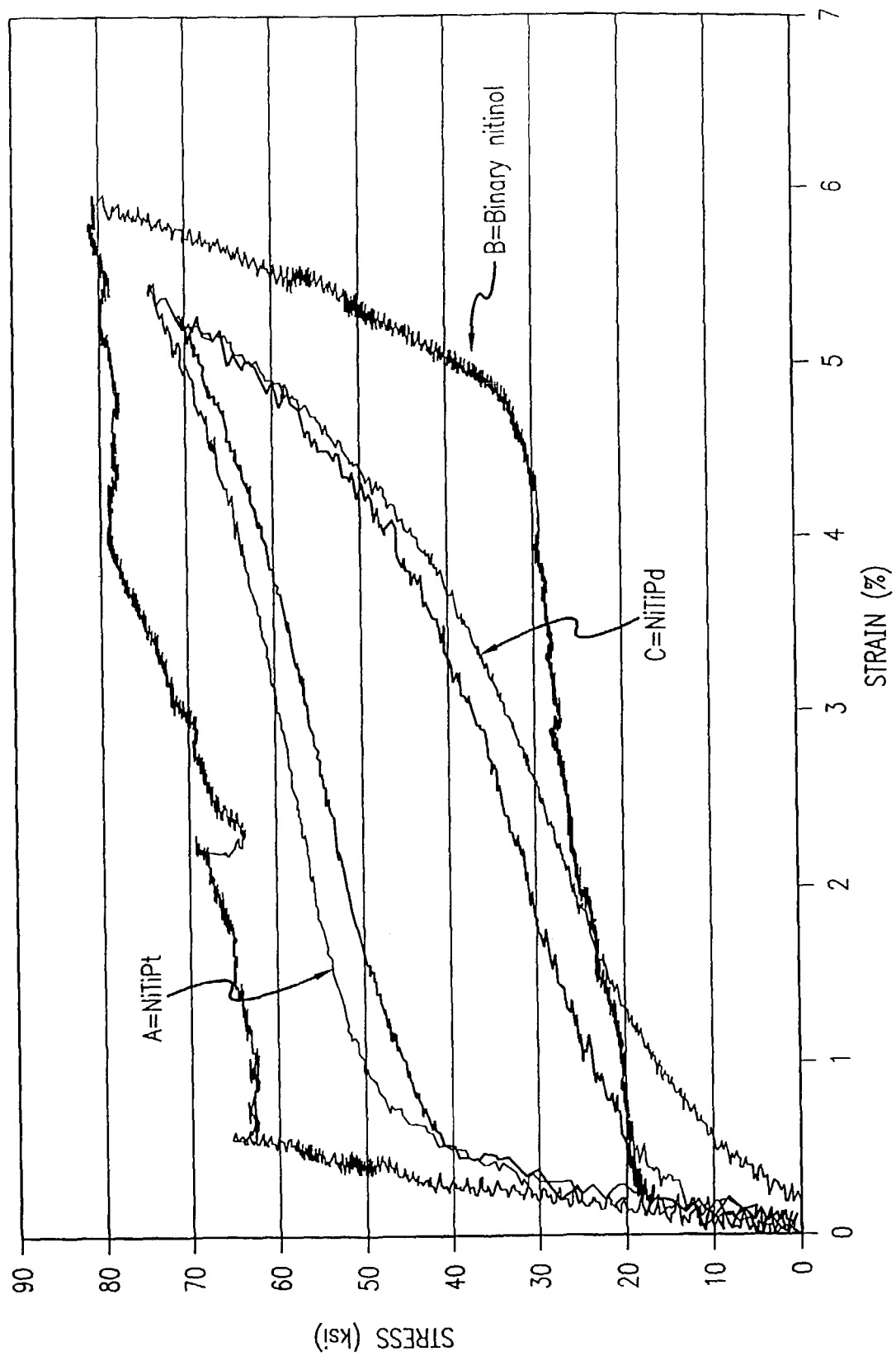
FIG. 3 is a set of stress-strain curves for binary nitinol, Ni—Ti—Pd, and Ni—Ti—Pt.

As is apparent from the plot of FIG. 3, the present invention nickel-titanium-palladium and nickel-titanium-platinum alloys have stress-strain curves that closely follow the hysteresis curve for non-linear pseudoelastic, binary nitinol. All three curves have essentially flat loading and unloading plateau stresses indicating the presence of a phase transformation that is characteristic of non-linear pseudoelastic metals. Hence, the present invention nitinol stent incorporates a ternary element, in these exemplary embodiments palladium or platinum, to improve radiopacity yet the materials' engineering capability (e.g., stress-strain behavior) is preserved. What has been missing heretofor is empirical evidence that this level of radiopacity can be achieved while preserving the engineering characteristics of these alloys.

The present invention further provides a nitinol wire or tube having improved radiopacity without reliance on increasing the wall thickness or strut thickness of the filter frame. Increasing wall or strut thicknesses detracts from the flexibility of the filtering device, which is detrimental to deliverability. Rather, the present invention radiopaque filter has a thin wall/strut thickness and/or strut cross-sectional area akin to a conventional stainless steel tube, and has comparable radiopacity to a stainless steel tube with a thin coating of gold. The wall/strut thickness is defined by the difference between the inside diameter and the outside diameter of the tube.

Moreover, conventional embolic filters rely on nickel-titanium alloy frames. Nickel-titanium is not known as a radiopaque material. The present invention frame made of a nickel-titanium alloy with one or more ternary elements renders the device radiopaque. This benefits the physician by enabling him or her to clearly visually locate the filter assembly downstream from the site of the ongoing interventional procedure.

The present invention frame is made from the radiopaque nitinol alloy described above, and the alloy is further fashioned such that is behaves linear pseudoelastically inside a patient's body lumen. In particular, in yet another process for manufacturing the frame and/or half frames, the laser cut nitinol tubing is preferably cold formed and specifically cold worked with no heat treatment such that it remains in a fully martensitic state in the body lumen. The cold working proceeds only at temperatures below the recrystallization temperature of the nitinol alloy. Next, the laser-cut nitinol tubing is cold worked to its desired expanded size. The desired expanded size is thus imparted or set into the laser cut tube.

Importantly, the laser-cut nitinol tubing is not heat treated to prevent generation of any loading or unloading plateaus in the stress-strain curve. In an alternative embodiment, the nitinol tubing may undergo limited heat treating for only very short durations at low temperatures. The present invention recognizes that a significant difference between linear pseudoelasticity and non-linear pseudoelasticity is the absence or presence, respectively, of stress-induced martensite. It also recognizes that in order to set a particular shape in nitinol, the nitinol must be heat treated at a relatively high temperature for a short period of time. Under normal circumstances, this material would then exhibit non-linear pseudoelasticity and therefore would undergo a reversible phase transformation from austenite to martensite. When setting a shape under standard conditions, for example, 550 degrees C. for 5 minutes, the nitinol exhibits essentially no springback; that is, its unconstrained shape after heat treatment is nearly identical to its constrained shape during heat treatment. The nitinol does not spring back to its original shape prior to heat treatment. At the other extreme, linear pseudoelastic nitinol with no heat treatment has 100 percent springback and always returns to its original, cold worked shape.

Springback is a continuous function between no heat treatment (100 percent springback) and ideal shape setting heat treatment (approximately zero percent springback). From an engineering perspective for design of nitinol based pseudoelastic devices, less springback is sometimes more favorable than more springback. However, in some circumstances, linear pseudoelasticity may be preferable to non-linear pseudoelasticity. Therefore, the present invention, in addition to contemplating cold-worked only nitinol, addresses that regime of heat treatment temperatures and times within which springback is adequately minimized to successfully impart a desired shape to the nitinol structure and within which the nitinol does not develop a stable and reversible martensitic phase.

In a preferred embodiment of the present invention, to achieve the linear pseudoelastic behavior, the binary nickel-titanium tubing has approximately 55.8 atomic percent nickel. The tubing preferably contains a minimum of approximately 38 percent cold working when measured by the reduction in cross-sectional area, and there is not to be any heat treatment following final cold reduction. As to the alternative embodiment, the present invention contemplates accumulated heat treatment of the tubing of up to 300 degrees C. for up to 5 minutes. Under ideal conditions, these process parameters should adequately ensure that the nitinol remains martensitic without a phase change under stress.

Figure 4:
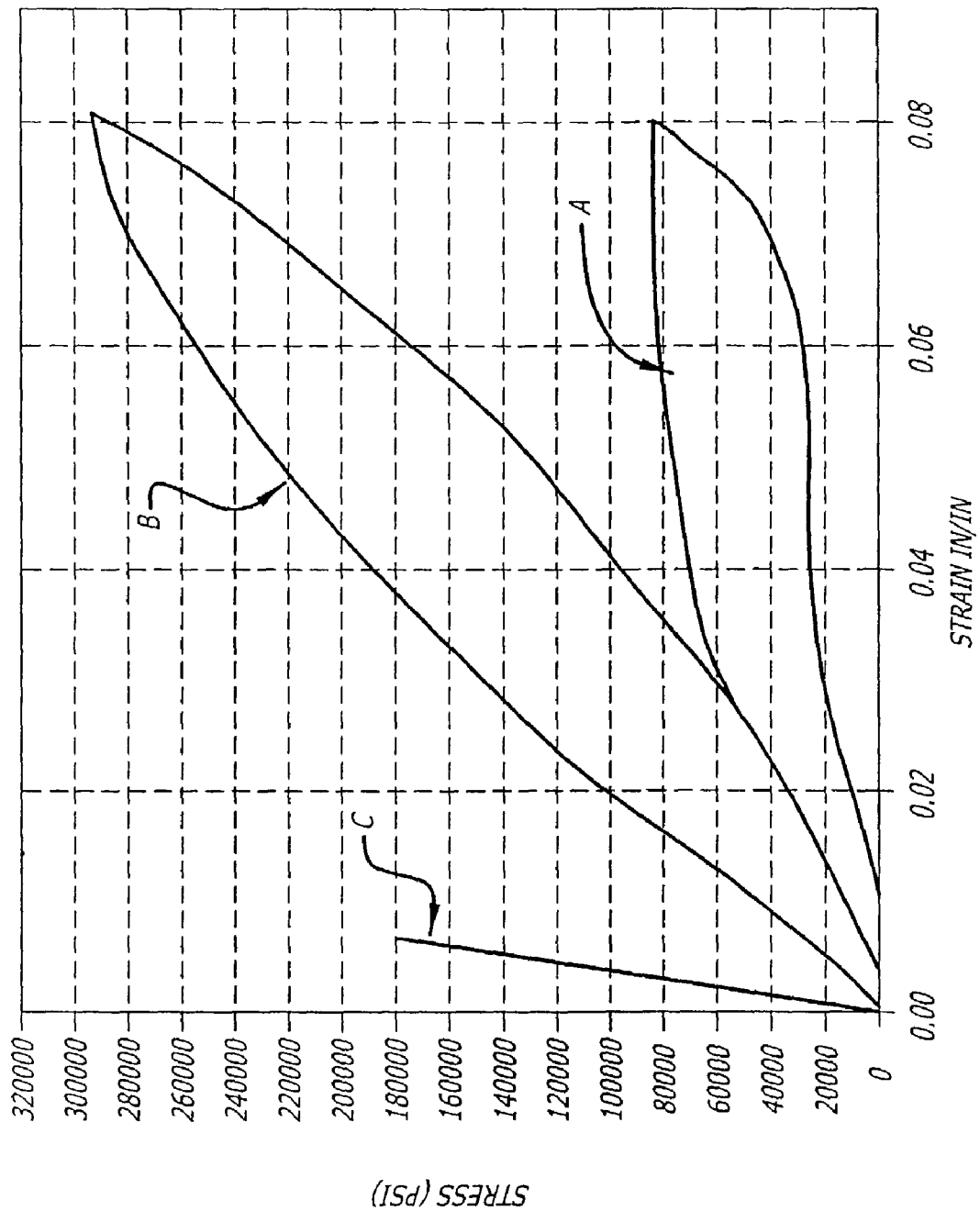
FIG. 4 is a set of stress-strain curves for conventional 316L stainless steel, linear pseudoelastic nitinol, and non-linear pseudoelastic nitinol.

To illustrate the foregoing points, FIG. 4 contains the elastic component of three idealized stress-strain curves for 316L stainless steel, linear pseudoelastic nitinol, and non-linear pseudoelastic nitinol. In a preferred embodiment, the radiopaque expandable frame of the present invention is formed partially or completely of alloys such as the linear pseudoelastic nitinol shown to have the stress-strain properties depicted in curve B or FIG. 4.

In FIG. 4, in an idealized curve A for a non-linear pseudoelastic nitinol, the relationship is plotted on x-y axes, with the x axis representing strain and the y axis representing stress. For illustrative purposes, the x and y axes are labeled in units of stress from zero to 320 ksi and strain from 0 to 9 percent, respectively.

In curve A, when stress is applied to a specimen of a metal such as nitinol exhibiting non-linear pseudoelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase (i.e., the stress-induced martensite phase). As the phase transformation progresses, the alloy undergoes significant increases in strain with little or no corresponding increases in stress. On curve A this is represented by upper, nearly flat stress plateau at approximately 70 to 80 ksi. The strain increases while the stress remains essentially constant until the transformation of the austenitic phase to the martensitic phase is complete. Thereafter, further increase in stress is necessary to cause further deformation. The martensitic metal first yields elastically upon the application of additional stress and then plastically with permanent residual deformation (not shown).

If the load on the specimen is removed before any permanent deformation has occurred, the martensite specimen elastically recovers and transforms back to the austenitic phase. The reduction in stress first causes a decrease in strain. As stress reduction reaches the level at which the martensitic phase transforms back into the austenitic phase, the stress level in the specimen remains essentially constant (but less than the constant stress level at which the austenitic crystalline structure transforms to the martensitic crystalline structure until the transformation back to the austenitic phase is complete); i.e., there is significant recovery in strain with only negligible corresponding stress reduction. This is represented in curve A by the lower stress plateau at about 20 ksi.

After the transformation back to austenite is complete, further stress reduction results in elastic strain reduction. This ability to incur significant strain at relatively constant stress upon the application of a load and to recover from the deformation upon the removal of the load is commonly referred to as non-linear pseudoelasticity (or superelasticity).

FIG. 4 also has a curve B representing the idealized behavior of linear pseudoelastic nitinol. Curve B generally has a higher slope or Young's Modulus than curve A for the non-linear pseudoelastic nitinol. Also, curve B does not contain any flat plateau stresses found in curve A. This stands to reason since the nitinol of curve B remains in the martensitic phase throughout and does not undergo any phase change. The same tension and release of stress cycle to generate curve A is used to generate curve B. To that end, curve B shows that increasing stress begets a proportional increase in reversible strain, and a release of stress begets a proportional decrease in strain. The areas bounded by curves A and B represent the hysteresis in the nitinol.

As apparent from comparing curve B to curve A in FIG. 4, with the use of linear pseudoelastic nitinol, the mechanical strength of the present invention medical device is substantially greater per unit strain than a comparable device made of non-linear pseudoelastic nitinol. Consequently, a major benefit is that smaller component parts such as struts can be used because of the greater storage of energy available in a linear pseudoelastic nitinol device. A small profile is one critical factor for crossing narrow lesions or for accessing remote and tortuous arteries.

FIG. 4 includes curve C which is the elastic behavior of a standard 316L stainless steel. Stress is incrementally applied to the steel and, just prior to the metal deforming plastically, decrementally released. It is provided here simply for comparison to curves A and B.

The polymeric material used for the filtering element includes, but is not limited to, polyurethane and Gortex, a commercially available material. Other possible suitable materials include ePTFE. The material can be elastic or inelastic. The wall thickness of the filtering element can be about 0.00050-0.0050 inch. The wall thickness may vary depending on the particular material selected. The material can be made into a cone or similar shape by blow-mold or dip-mold technology. The openings can be any shape or size. A laser, a heated rod, or other piercing or cutting processes known in the art can create the perfusion openings in the filter material. The holes would of course be properly sized to catch the particular size of embolic debris of interest. Holes can be lazed in a spiral pattern or the like which aids in trapping the debris during closure of the filter. Additionally, the filter material can have a "set" imparted thereto much like the "set" used in dilatation balloons to make the filter element re-wrap more easily when transforming into the collapsed position.

The material employed to manufacture the filtering element 26 can be modified thermoplastic polyurethane elastomer. Such elastomers can be prepared by reacting polyester or polyester diol, a short-chain diol, a diisocyanate, and a substituted diol. The isocyanate portion is commonly referred to as the hard segment and the diol as the soft segment. It has been found that such a material offers excellent flexibility along with resistance to broad temperature ranges or tough end-use environments. Moreover, the presence of substituted diol makes the urethane non-blocking (non-sticking) and thus desirable in many medical applications including filtering and embolic protection systems use.

The filter element can be made from thermoplastic polyurethane elastomers (TPU) made with substituted "diol." TPUs have both the mechanical as well as physical properties that are highly desirable in medical device applications. Filter element made with substituted "diol" TPU is non-blocking (non-sticking) and thus self adherence or undesirable adherence to other structures is minimized. Such a characteristic is a key to the effectiveness of a filter or other medical device as repeated manipulation and expansion and compression is common in the use of a filter. Thus, a filter made with modified TPUs (for example, modified PELLATHANE™), can consistently provide a surface or cavity for receiving matter and can be moved and expanded or contracted in vasculature to effectively accomplish its filtering function.

A combination of high tensile strength and high elongation of modified thermoplastic polyurethane elastomers contemplated makes the material well-suited for dip forming or molding applications. Notably, conventional methods such as blow molding inherently creates stresses and tensions in the element being blow molded.

In certain applications, it may be desirable to apply a biocompatible lubricous coating to the filtering device. Such a lubricous coating can be Dow Corning 360 or other known biocompatible coatings. The coating can aid in the use of the filtering device, for example, by facilitating deployment and manipulation. The filter element itself can be coated as well as the frame or cage to which it is attached.

The materials used for the restraining sheath 30 can be made from polymeric material such as cross-linked HDPE. This sheath can alternatively be made from a material such as polyolifin which has sufficient strength to hold the compressed filter assembly and has relatively low frictional characteristics to minimize any friction between the filtering assembly and the sheath. Friction can be further reduced by applying a coat of silicone lubricant, such as MICRO-GLIDE®, to the inside surface of the restraining sheath before the sheaths are placed over the filtering assembly.

It should be appreciated that the embodiments of the embolic filtering device described herein are by way of example only and not by way of limitation. Also, while the present invention is described in detail as applied to an artery of the patient, those skilled in the art appreciate that it can also be used in a variety of arteries or other body lumens, such as the coronary arteries, carotid arteries, renal arteries, saphenous vein grafts and other peripheral arteries. Additionally, the present invention can be used when a physician performs any one of a number of interventional procedures, such as balloon angioplasty, laser angioplasty or atherectomy, which generally requires an embolic filtering device to capture embolic debris created during the procedure.

Further modifications and improvements may additionally be made to the device and method disclosed herein without departing from the scope of the present invention. Accordingly, it is not intended that the invention be limited, except as by the appended claims.

What is claimed:

1. A radiopaque, expandable frame for an embolic filtering device used to capture embolic debris in a body lumen, the frame comprising:

two half frames having respective proximal and distal portions, the half frames being movable between an unexpanded position and an expanded position, wherein each half frame includes:

first and second control arms, a partial hoop extending in a circumferential direction between the first and second control arms, and a substantially D-shaped flex region extending substantially perpendicular to the partial hoop and located at or near an apex of the partial hoop, the partial hoops of the first and second control arms defining a circular hoop;

wherein each of the first and second control arms include a proximal angled portion extending away from a longitudinal axis of the frame and a distal portion configured to contact a body lumen wall and extending substantially parallel to the longitudinal axis;

a polymeric filtering element having an expandable proximal end and a substantially closed distal end disposed on the half frames, wherein the polymeric filtering element includes a plurality of holes formed in rows extending between the proximal end and the distal end with the holes being arranged such that holes in adjacent rows are offset relative to one another; and a collar disposed proximal to the filtering element, wherein:

the proximal portions of the half frames are coupled to the collar;

the frame is formed of a cold-worked linear pseudoelastic alloy, the alloy having a martensitic phase in the unexpanded and expanded position; and the alloy further includes at least one ternary element selected from the group of elements consisting of: iridium, platinum, gold, rhenium, tungsten, rhodium, tantalum, silver, ruthenium, or hafnium.

2. The radiopaque, expandable frame of claim 1, wherein the linear pseudoelastic alloy includes about 30 to 52 atomic percent titanium, and a balance of nickel.

3. The radiopaque, expandable frame of claim 1, wherein the frame has received limited heat treating so that the frame is linearly pseudoelastic when deployed inside a body lumen and does not exhibit a stress plateau.

4. The radiopaque, expandable frame of claim 1, wherein the frame is more radiopaque than an identical expandable frame made from a binary nickel-titanium alloy.

5. The radiopaque, expandable frame of claim 1, wherein the austenite start temperature (As) of the alloy is greater than an ambient temperature inside the body lumen.

6. A radiopaque, expandable frame for an embolic filtering device used to capture embolic debris in a body lumen, the frame comprising:

a first half frame adapted to move between an unexpanded position and an expanded position, the first half frame having first and second control arms and a partial hoop extending in a circumferential direction between the first and second control arms;

a second half frame connected to the first half frame, the second half frame having first and second control arms and a partial hoop extending in a circumferential direction between the first and second control arms, wherein:

the partial hoops of the first and second half frames defining a circular hoop; and each of the first and second control arms of the first and second half frames includes a proximal angled portion that extends axially and radially outwardly and a distal portion extending axially that is configured to contact a body lumen wall;

a substantially D-shaped flex region associated with at least one of the first and second half frames and extending substantially perpendicular to and located at or near an apex of one of the partial hoops;

a polymeric filtering element having an expandable proximal end and a substantially closed distal end disposed on the half frames, wherein the polymeric filtering element includes a plurality of holes formed in a spiral pattern such that holes in adjacent rows are offset relative to one another; and a collar, wherein:

the first half frame and the second half frame cooperatively deploy a filtering element:

the collar is disposed proximal to the filtering element;

a proximal portion of the first and second half frames is coupled to the collar; and at least one of the first and second half frames are formed of a cold-worked linear pseudoelastic alloy having a martensitic phase in the unexpanded and expanded position, and the alloy further includes a ternary element selected from the group of elements consisting of: iridium, platinum, gold, rhenium, tungsten.

7. The radiopaque, expandable frame of claim 6, wherein the linear pseudoelastic, nickel-titanium alloy frame includes at least one of a wire, a tube, and a braided wire.

8. The radiopaque, expandable frame of claim 6, wherein the frame is more radiopaque than an identical expandable frame made from a binary nickel-titanium alloy.

9. The radiopaque, expandable frame of claim 6, wherein the atomic percent of titanium is greater than or equal to 46 and less than or equal to 52.

10. The radiopaque, expandable frame of claim 6, wherein the austenite start temperature (As) of the alloy is greater than 37 degree C.

11. The radiopaque, expandable frame of claim 6, wherein the linear pseudoelastic alloy frame when deployed in the body lumen exhibits no stress plateaus in a stress-strain curve.

12. The radiopaque, expandable frame of claim 6, wherein at least one of the first and second half frames has received limited heat treating so that the linear pseudoelastic alloy frame when deployed inside a body lumen does not exhibit a stress plateau.

13. The radiopaque, expandable frame of claim 6, wherein at least one of the first and second half frames assumes a shape imparted by cold forming.

14. A radiopaque, expandable frame for an embolic filtering device used to capture embolic debris in a body lumen, the frame comprising:

a first half frame adapted to move between an unexpanded position and an expanded position, the first half frame having first and second control arms and a partial hoop extending in a circumferential direction between the first and second control arms;

a second half frame adapted to move between an unexpanded position and an expanded position connected to the first half frame, the second half frame having first and second control arms and a partial hoop extending in a circumferential direction between the first and second control arms, wherein:

the partial hoops of the first and second half frames defining a circular hoop; and each of the first and second control arms of the first and second half frames includes a proximal angled portion that extends axially and radially outwardly and a distal portion extending axially that is configured to contact a body lumen wall;

a substantially D-shaped flex region associated with each of the first and second half frames and extending substantially perpendicular to and located at or near an apex of the partial hoops;

a polymeric filtering element disposed on the half frames, the polymeric filtering element having an exterior surface defining a substantially parabolic exterior surface in an expanded position, wherein the polymeric filtering element includes a rounded, atraumatic proximal edge surface, an elongate distal portion extending from the substantially parabolic exterior surface, and a plurality of holes formed in the polymeric filtering element in a spiral pattern such that holes in adjacent rows are offset relative to one another; and a collar, wherein:
the first half frame and the second half frame cooperatively deploy a filtering element;
the collar is disposed proximal to the filtering element;
a proximal portion of the first and second half frames is coupled to the collar; and
at least one of the first and second half frames are formed of a cold-worked linear pseudoelastic alloy having a martensitic phase in the unexpanded and expanded position, and the alloy further includes a ternary element selected from the group of elements consisting of: iridium, platinum, gold, rhenium, tungsten.

15. The radiopaque, expandable frame of claim 14, wherein the linear pseudoelastic alloy frame when deployed in the body lumen exhibits no stress plateaus in a stress-strain curve.

16. The radiopaque, expandable frame of claim 14, wherein at least one of the first and second half frames has received limited heat treating so that the linear pseudoelastic alloy frame when deployed inside a body lumen does not exhibit a stress plateau.

* * * * *